US011313821B2

(12) United States Patent
Zhao

(10) Patent No.: US 11,313,821 B2
(45) Date of Patent: Apr. 26, 2022

(54) SENSOR

(71) Applicant: GRIFFITH UNIVERSITY, Nathan (AU)

(72) Inventor: Huijun Zhao, Nathan (AU)

(73) Assignee: GRIFFITH UNIVERSITY, Nathan (AU)

( * ) Notice: Subject to any disclaimer, the term of this patent is extended or adjusted under 35 U.S.C. 154(b) by 44 days.

(21) Appl. No.: 16/626,888

(22) PCT Filed: Jun. 28, 2018

(86) PCT No.: PCT/AU2018/050662
§ 371 (c)(1),
(2) Date: Dec. 27, 2019

(87) PCT Pub. No.: WO2019/000040
PCT Pub. Date: Jan. 3, 2019

(65) Prior Publication Data
US 2020/0124554 A1    Apr. 23, 2020

(30) Foreign Application Priority Data

Jun. 29, 2017 (AU) ................................ 2017902515

(51) Int. Cl.
*B01L 3/00* (2006.01)
*G01N 27/12* (2006.01)
(Continued)

(52) U.S. Cl.
CPC ......... *G01N 27/125* (2013.01); *B01D 63/087* (2013.01); *B01D 69/02* (2013.01);
(Continued)

(58) Field of Classification Search
CPC ...... B01D 63/087; B01D 63/08; B01D 69/02; B01D 69/00; B01D 71/36; B01D 71/32;
(Continued)

(56) References Cited

U.S. PATENT DOCUMENTS 4,209,299 A    6/1980   Carlson
5,131,260 A *  7/1992   Brand ................ G01N 33/0054
                                                        73/23.2
(Continued)

FOREIGN PATENT DOCUMENTS

CN        105651826 A    6/2016
JP        H11118782 A    4/1999

OTHER PUBLICATIONS

Li et al., "A Gas-permeable Membrane-based Conductivity Probe Capable of In Situ Real-time Monitoring Ammonia in Aquatic Environment", Environ. Sci. Technol. 2017, 51, Published on Oct. 25, 2017, pp. 15.
(Continued)

*Primary Examiner* — Christine T Mui
(74) *Attorney, Agent, or Firm* — EcoTech Law Group, P.C.

(57) ABSTRACT

A sensor for the in situ detection of a target chemical species, comprising a gas permeable membrane having a sampling side and an opposing analytical side, wherein the sampling side of the membrane is capable of receiving a sample and the membrane is permeable to target chemical species present in the sample. A weak acid or a weak base is in contact with the analytical side of the membrane, and a conductivity detector is in contact with the weak acid or weak base. In use, target chemical species present in the sample permeate through the membrane and react with the weak acid or weak base, producing ionic species and changing the conductivity.

12 Claims, 20 Drawing Sheets

(51) Int. Cl.
*B01D 63/08* (2006.01)
*B01D 69/02* (2006.01)
*B01D 71/36* (2006.01)
*G01N 33/18* (2006.01)
*B01D 63/02* (2006.01)

(52) U.S. Cl.
CPC ............... *B01D 71/36* (2013.01); *B01L 3/50* (2013.01); *G01N 33/1886* (2013.01); *B01D 2325/38* (2013.01); *B01L 2200/025* (2013.01); *B01L 2200/0689* (2013.01); *B01L 2300/0645* (2013.01); *B01L 2300/0663* (2013.01); *B01L 2300/0681* (2013.01); *B01L 2300/12* (2013.01)

(58) Field of Classification Search
CPC .... B01D 71/06; G01N 33/1886; G01N 33/18; B01L 3/50; B01L 2200/025; B01L 2200/0689; B01L 2300/0645; B01L 2300/0663; B01L 2300/0681; B01L 2300/12
USPC .......................................................... 422/90
See application file for complete search history.

(56) References Cited

U.S. PATENT DOCUMENTS

| 5,643,799 | A | 7/1997 | Atwater et al. |
| 6,090,267 | A | 7/2000 | Hansen et al. |
| 7,103,481 | B2 * | 9/2006 | Negri ................. G01N 33/0031 702/22 |
| 7,437,248 | B2 * | 10/2008 | Sihalla .................... G01N 1/14 702/22 |
| 9,651,374 | B1 | 5/2017 | Wingo et al. |
| 2014/0348593 | A1 | 11/2014 | Kawahara et al. |

OTHER PUBLICATIONS

International Search Report and Written Opinion for International Application No. PCT/AU2018/050662 dated Sep. 21, 2018, pp. 11.
Extended European Search Report received for European Application No. 18824367.9, dated Jun. 21, 2021, 13 Pages.
M.T. Oms et al., Preconcentration by flow reversal in conductometric sequential injection analysis of ammonium, Electroanalysis, Apr. 1996, pp. 387-390, vol. No. 8, VCH Publishers, Palma de mallorca Spain.
Vanu Pattawa et al., Down scaled Kjeldahl digestion and flow injection conductometric system for determination of protein content in some traditional northern Thai foods, Food Chemistry, Mar. 8, 2017, pp. 572-577, vol. No. 230, Elsevier Ltd, Netherlands.

* cited by examiner

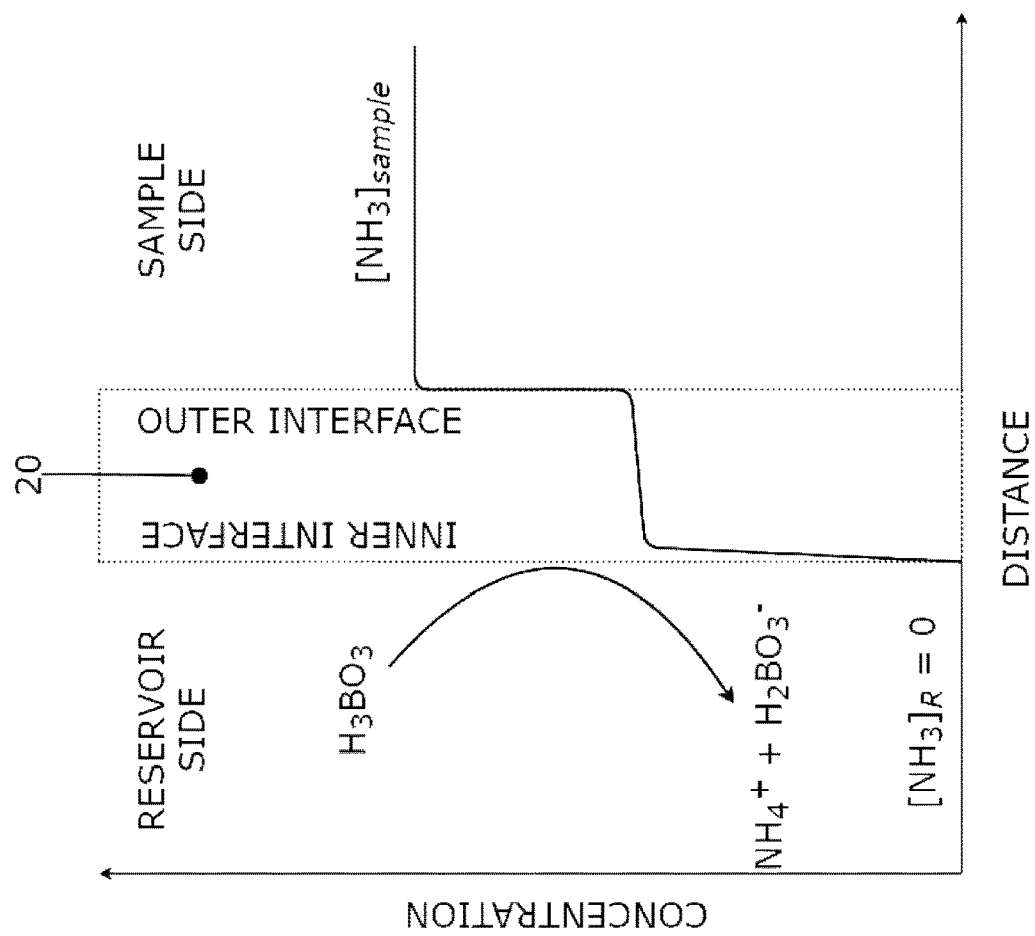
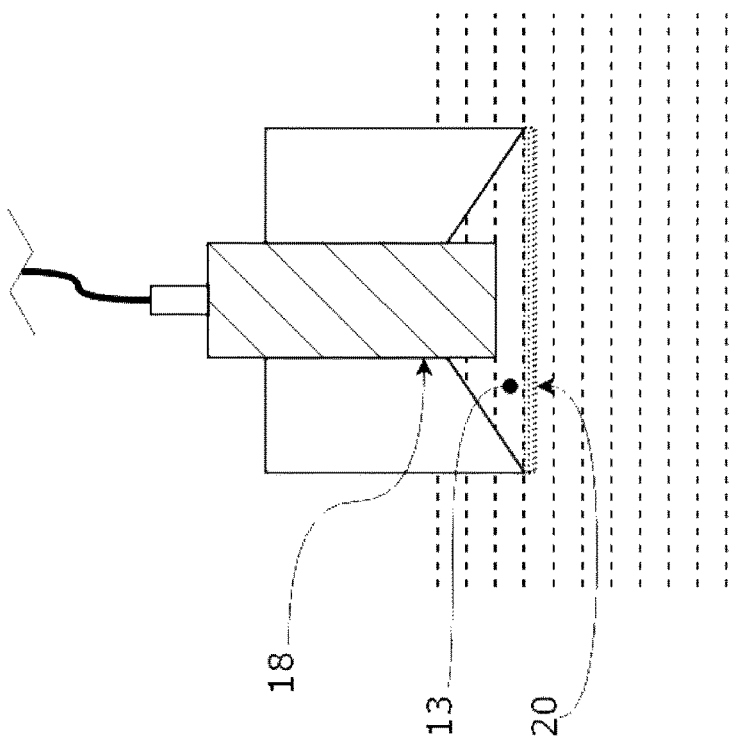
FIGURE 2B
FIGURE 2A

The average N-NH$_3$ concentration calculated from MEAP is 286.1 µg L$^{-1}$ over experiment period.

Table S1 Caculation in Figure 3c

| Added [NH$_3$] (µg L$^{-1}$) | 102 | 510 | 1020 | 2040 | 3060 | 4080 |
|---|---|---|---|---|---|---|
| R$_{ct}$ (µS cm$^{-1}$ min$^{-1}$) | 0.133 | 0.674 | 1.44 | 2.70 | 4.31 | 5.61 |
| K (µS cm$^{-1}$ min$^{-1}$ µg$^{-1}$ L) | | | 0.00135 | | | |
| Determined $\overline{[NH_3]}$ (µg L$^{-1}$) | 98.52 | 499.3 | 1066 | 2000 | 3192 | 4155 |
| Deviation (%)* | -3.41% | -2.10% | 4.51% | -1.96% | 4.31% | 1.84% |

* $Deviation\ (\%) = \dfrac{\overline{[NH_3]} - \{Added\ [NH_3]\}}{\{Added\ [NH_3]\}} \times 100\%$

Table S2

| Probe | K (25 °C) (µS cm$^{-1}$ min$^{-1}$ µg$^{-1}$ L) | Temperature Correction for EC Detector (µS cm$^{-1}$) | Temperature Correction for Probe Constant (K) (µS cm$^{-1}$ min$^{-1}$ µg$^{-1}$ L) |
|---|---|---|---|
| GPMCP#1 | 0.00135 | $\sigma_{25} = \sigma_T + 1.08 \times (25 - T)$ | $K(T) = 2.65 \times 10^{-5} T(°C) + 6.85 \times 10^{-4}$ |
| GPMCP#2 | 0.00146 | $\sigma_{25} = \sigma_T + 1.10 \times (25 - T)$ | $K(T) = 5.13 \times 10^{-5} T(°C) + 1.78 \times 10^{-4}$ |
| GPMCP#3 | 0.00123 | $\sigma_{25} = \sigma_T + 1.12 \times (25 - T)$ | $K(T) = 3.50 \times 10^{-5} T(°C) + 2.85 \times 10^{-4}$ |

FIGURE 13

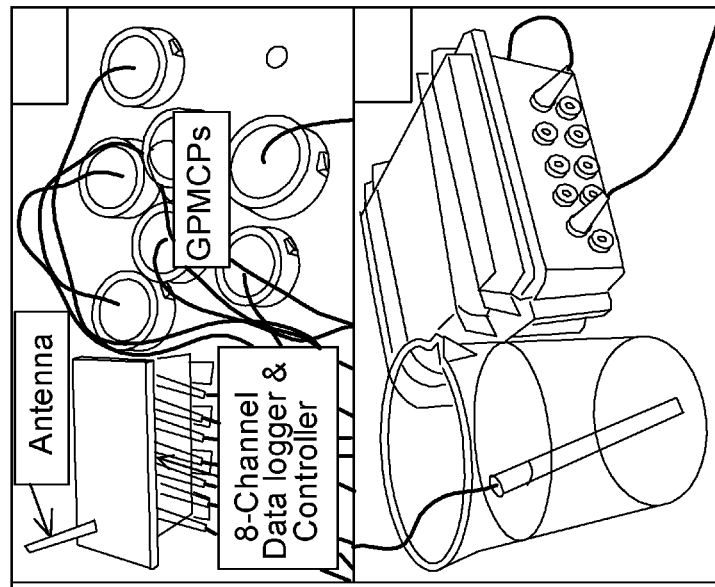
Figure 14B
Figure 14C
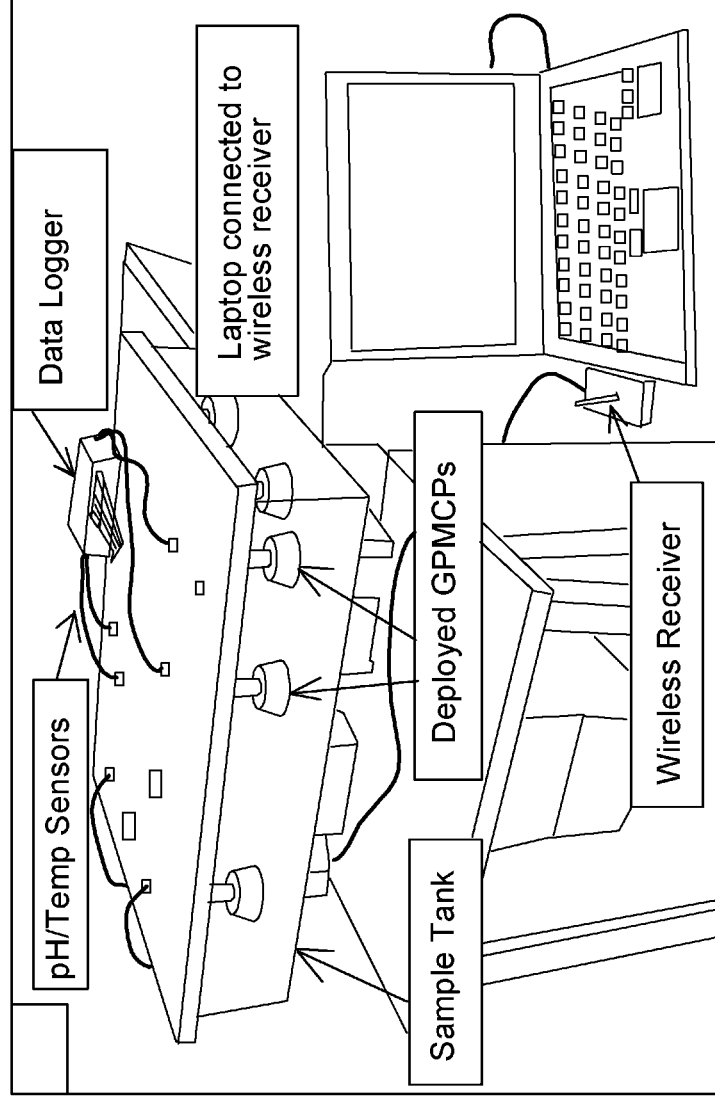
Figure 14A

SENSOR

RELATED APPLICATION

This application claims the benefit from International Application No. PCT/AU2018/050662, which was granted an International filing date of Jun. 28, 2018, which in turns claims priority to Australia application no. 2017902515, filed Jun. 29, 2017, and are incorporated herein by reference for all purposes.

TECHNICAL FIELD

The present invention relates to a sensor for the detection of chemical species in aquatic, air or agricultural environments. In one embodiment, the chemical species is free ammonia, and the sensor detects free ammonia in aquatic, air or agricultural environments.

BACKGROUND

The detection of chemical species in the environment can provide important information regarding ecosystem wellbeing, and critical data for effective remediation and better ecosystem management practice. Ammonia is a chemical species that can be detected in the environment. Ammonia is found ubiquitously in natural waters and plays an essential role in the growth, metabolism and reproduction of aquatic organisms. It has been well established that ammonia as a major form of nitrogen-based nutrients plays a key role in the ecological health of rivers, estuaries and marines waters. The determination of the amount of nutrients such as ammonia in these systems can assist in planning their ongoing management. It can therefore be advantageous to detect the chemical species ammonia in the environment.

The amount of a chemical species in the environment can be measured and monitored to ensure that any use of that chemical is kept to minimum required amount. One such chemical that is desirably used in the lowest required amount is fertilizer. Currently, fertilizer production accounts for about 2% of total global energy consumptions. However, over 60% of the applied fertilizer is wasted via leaching and vaporisation processes into water and atmosphere, in some instances causing serious eutrophication and fog haze pollutions to waterways and atmosphere, and substantial economic losses. It is desirable to provide a system for measuring fertilizer use and fertilizer loss. Some fertilizers comprise ammonia. An effective assay technique applicable for large-scale, long-term, continuous monitoring of soil ammonia loss may enable an improved fertilization practice to minimize the waste of the applied fertilizer, and protect aquatic and atmospheric environments.

Existing sensors for detecting target chemical species make use of a variety of sensing techniques. Ammonia detection methods include, for example, the traditional standard Nessler method, fluorescence methods, chemiluminescence methods, ion-selective electrode methods and biosensors and other types of sensors. It is desirable to provide an improved sensor that can detect a target chemical species such as ammonia. The data from the sensor can be used to assist in the management of the chemical species, such as ammonia, in the environment.

SUMMARY OF INVENTION

According to a first aspect of the invention there is provided a sensor for the in situ detection of a target chemical species, the sensor comprising:

a gas permeable membrane having a sampling side and an opposing analytical side, wherein the sampling side of the membrane is capable of receiving a sample and the membrane is permeable to target chemical species present in the sample;

a weak acid or a weak base in contact with the analytical side of the membrane;

a conductivity detector in contact with the weak acid or weak base, the conductivity detector for measuring the conductivity on the analytical side of the membrane;

wherein in use target chemical species present in the sample permeate through the membrane and react with the weak acid or weak base thereby producing ionic species, the ionic species changing the conductivity at the analytical side of the membrane.

In an embodiment, the target chemical species is free ammonia and a weak acid is present on the analytical side of the membrane. When the free ammonia in the sample permeates through the membrane and reacts with the weak acid, ammonium ions are produced. The ammonium ions increase the conductivity at the analytical side of the membrane. The increased conductivity can be measured by the conductivity detector. The measurement can be recorded as data. The data can be used in the management of the amount of ammonia in the sampled environment.

Thus, according to a second aspect of the invention there is provided a sensor for the in situ detection of a free ammonia, the sensor comprising:

a gas permeable hydrophobic PTFE membrane having a sampling side and an opposing analytical side, wherein the sampling side of the membrane is capable of receiving a sample and the membrane is permeable to free ammonia present in the sample;

boric acid on the analytical side of the membrane;

a conductivity detector in contact with the boric acid, the conductivity detector for detecting a change in conductivity on the analytical side of the membrane;

wherein in use free ammonia present in the sample permeates through the membrane and reacts with the boric acid thereby producing positively charged ammonium ions $NH_3^+$ and negatively charged dihydrogen borate $H_2BO_3^-$, the ionic species increasing the conductivity at the analytical side of the membrane.

The following description applies to both the first and second aspects of the invention, unless the context makes clear otherwise.

Many existing sensors are incapable of performing real-time, in situ/online continuous monitoring of instantaneous ammonia concentration or average ammonia concentration during a deployment period. The sensor of the present invention may in some embodiments allow for the instantaneous monitoring of ammonia concentration in a sample, and or it may allow the monitoring of an average ammonia concentration during a deployment period. The sensor can in some embodiments provide a sensitive, accurate and reliable means for the large-scale long-term continuous monitoring of ammonia in e.g. drinking water or aquatic environments or to monitor soil ammonia evaporation.

While ammonia is described herein as an exemplary target chemical species, it should be understood that the sensor can be modified to detect other chemical species.

By in situ detection it is meant that the sensor can generate data from the sampling position in which it is located. The data generated by the sensor can be collected, analysed and or recorded while the sensor is in position. This is an advantage over prior art method that may require that a sample of e.g. water be taken for subsequent analysis of it e.g. in a laboratory.

The conductivity measurements taken by the sensor can be fed to a computer running software that analyses the data. The computer can be a data acquisition unit. The data can be analysed to covert the conductivity measurement into a equivalent chemical concentration. For example, a conductivity concentration caused by ammonium ions, can be converted to an equivalent ammonia concentration.

The sensor data analysis can provide information as to the amount of a target chemical species present in a sample location. The amount of the target chemical species can be calculated as an average concentration of the target chemical species, by taking a series of measurements which are averaged over time. When the conductivity of a single measurement, or an average measurement, changes relative to a pre-determined threshold, the computer analysing the sample data can generate a signal or an alert. The signal or alert can indicate to an operator that there is too much or not enough of a target chemical species in the sample. If there is too much of a target chemical species in a sample, this might cause the operator to take some remedial action. The remedial action might be to stop an activity that is causing the chemical species to be in the sample, or to increase another activity that decreases the amount of chemical species in the sample. If there is not enough of a target chemical species in a sample, this might cause the operator to take some remedial action. The remedial action might be to increase an activity that increases the amount of chemical species in a sample or to increase another activity that increases the amount of chemical species in the sample.

The sensor can generate data in real time which can allow the operator monitoring the data to react quickly in response to the data. In an embodiment, the sensor is built into an overall process control system which includes automatic operation of a chemical process. The chemical process could be the monitoring of the amount of a chemical in drinking water. In this embodiment, when the target chemical species in the drinking water is detected above or below a predetermined threshold level, the system can automatically stop or slow (or increase) a process that is causing the buildup of the chemical species.

The conductivity detector (sometimes referred to as EC Detector) can comprise electrodes. There can be a plurality of electrodes. In an embodiment there are four electrodes. The electrodes can be embedded in the sensor so as to allow the electrodes to take a reading of the conductivity at the weak acid or weak base side of the sensor. The weak acid or weak base is sometimes referred to as a reactive receiving phase. The change in conductivity is related to the generation of ionic species at the analytical side of the membrane. A formula can be developed that correlates the change in conductivity to the formation of ions, which is in turn correlated to the amount of target chemical species on the sampling side of the membrane. A change as low as about 0.5, about 0.8, about 1 or about 2 µS/cm in conductivity can be detected by the sensor.

The background conductivity of the weak acid or the weak base should be very low so that any changes in conductivity as a result of reaction with target chemical species can be readily detected by the sensor. In an embodiment, prior to use of the sensor the background conductivity of the weak acid or weak base is not more than about 20, about 30, about 40, about 50, about 60 or about 70 µS/cm. In an embodiment, prior to use of the sensor the background conductivity of the weak acid or weak base has a conductivity of at most about 450, about 500 µS cm$^{-1}$. In an embodiment, the weak acid is boric acid. In an embodiment, the weak base is glycocyamine.

The weak acid or weak base can be in a reservoir in the sensor. The reservoir is on the analytical side of the membrane. There can be a volume of at least about 0.05, about 0.1, about 0.5, about 1, about 2, about 5 or about 10 mL of the weak acid or weak base in the reservoir. The concentration can be at least about 0.1, about 0.2, about 0.5, about 0.8 or about 1 mole L$^{-1}$. A small amount of weak acid or weak base can make the sensor very sensitive to changes in the conductivity. The greater the volume of weak acid or weak base that is used, the less sensitive the sensor can be. However, a large volume of weak acid or base will allow the sensor to be used for a longer period of time before the reservoir of weak acid or weak base needs to be replenished. The weak acid or base in the sensor can be replenished while it is in situ. Alternatively, the sensor can be removed and replaced once the weak acid or weak base has been used.

This sensor and system as described may possess high sensitivity due to the accumulative nature of the processes. In addition, the conductivity measurement may be capable of picking up the conductivity changes in sub-micro S scale caused by very low concentration of the produced ammonium in the reactive receiving phase. In an embodiment, the sensor can detect a target chemical species in a sample at a concentration of at least about 0.2, about 0.5, about 1, about 10, about 20 or about 30 ppb. The detection limit of the sensor can depend on the specifications of the device and experimental conditions. For a given sensor and experimental conditions, the sensitivity increases as the deployment time increased. Sensitivity is important for environmental monitoring applications as the targeted species are often in low concentrations. The sensor can be capable of directly determining at least about 1, 5 or about 10 µg L$^{-1}$ of free ammonia. The exposed area of the sampling side of the membrane can be at least about 1, about 2, about 3, about 4, about 5, about 6, about 7, about 8, about 9 or about 10 cm$^2$. A sensor with a higher ratio of exposed membrane area to weak acid or weak base receiving phase volume may possess higher sensitivity, but lower upper linear range and shorter maximum deployment time.

The sensor can include a temperature sensor which measures the temperature at which the sample is taken. The temperature can be used in the formula used to correct the measured conductivity and sensor constant. The sensor can also include a pH sensor which measure the pH of the sample. The pH reading can be used to calculate the chemical concentration e.g. the ammonium concentration in based on the determined ionic concentration e.g. the ammonium concentration.

The membrane can be a gas permeable membrane. The membrane can be at most about 0.05, about 0.1 or about 0.3 mm in thickness. The membrane can have any diameter as required by the housing, for example, at least about 0.2, about 0.4 or about 0.6 mm or larger. The membrane can have an average pore size of at most about 0.1, about 0.2, about 0.3 or about 0.5 µm. The membrane can have a porosity of at least about 75, about 85 or about 90%. The membrane can be selected to allow selective permeation of the target chemical species. The membrane can be a PTFE (Teflon) membrane. The membrane can be selected to selectively permeate free ammonia (NH$_3$). In which case the membrane can be a hydrophobic membrane. The semi-permeable PTFE membrane permeates only small gaseous molecules which eliminates or at least reduces the vast majority of potential interference species, especially, the basic species such as OH⁻ in an aqueous media. Some dissolved $CO_2$ may permeate through the membrane into the receiving phase of weak acid. However, this should not affect the measured analytical signal (conductivity) as the reactive receiving phase used in this embodiment is an acid and the permeated $CO_2$ would remain in its molecular form in such an acidic medium.

The sensor can be located in one of an aquatic, atmospheric and agricultural environment. The aquatic environment can be selected from one of a river, stream, pond, reservoir and other body of water. The water can be fresh water, saltwater, grey water, waste water or other type of water. The water can be intended as drinking water. The water can be passing over the sensor surface i.e. the water can be flowing. The water can be dripping or sporadically reaching the sampling surface. The water can be in full contact with the sampling surface e.g. the sensor is under the water. The sensor can be moving under the water. The movement could be by pulling the sensor along behind a moving vehicle such as a boat. The atmospheric environment in which the sensor can be used is air. The sensor can be suspended in the air e.g. at a weather station. The agricultural environment can be soil, and the sensor can be arranged close to the soil so that the target chemical species is able to contact the sampling side of the sensor membrane.

The sensor can be deployed and left in position for a period of time sufficient for a reading to be taken. In an embodiment, the sensor can be immersed into a body of water for a period of time sufficient for a reading to be taken. Conductivity readings can be taken by the sensor continuously. Conductivity readings can be taken by the sensor at pre-determined time intervals. The readings can be taken at least about every 1, 2, 3, 4 or 5 seconds or at least about every 1, 2, 3, 4 or 5 minutes. The reading intervals can be every few seconds, minutes, every few hours, once per days, once per week or once per month. Optionally, the sensor is placed into position and is left permanently. The sensors can be connected to an electronic device. The connection to the electronic device can be e.g. wiring, or a remote connection such as Bluetooth. The electronic device can be a computer. The computer can be running software that analyses the data from the sensors.

A series of sensors can be arranged in a sampling area. The sensors can be arranged in a grid formation. The sensors can be supported by a grid such as a metal frame. The sensors can be spaced from one another laterally and or horizontally. In an aqueous environment, the sensors can be arranged at different depths. The sensors can be suspended in water from a surface floating device. If a series of sensors is used, the arrangement of the sensors can provide some indication as to where the target chemical species is coming from, e.g. a particular outlet in a wastewater treatment plant. The indication of where a target chemical species is being generated might be deducible from the sensor data, because one sensor in the series may report a higher reading of the target chemical species than the other sensors in the series.

Thus, in a third aspect of the invention there is provided a system for the in situ detection of a target chemical species in water, the system comprising a support under the water for supporting a plurality of sensors in accordance with the present disclosure;
a floater on the surface of the water from which the plurality of sensors depend,
an anchor to keep the plurality of sensors under the water;
a data acquisition unit for receiving data from the plurality of sensors;

wherein the plurality of sensors are spaced from one another under the water in a series so that a 3-dimensional profile of the concentration of the target chemical species in the water can be formed from the data received by the data acquisition unit.

In a fourth aspect there is provided a system for the in situ detection of a target chemical species, the system comprising at least one sensor in accordance with the present disclosure;
a data acquisition unit for receiving data from the at least one sensor; a process that is capable of generating the target chemical species, wherein the at least one sensor is arranged so as to detect the target chemical species if it is generated in the process;
a pre-determined threshold concentration of the target chemical species programmed into the data acquisition unit;
wherein the data acquisition unit compares any detected concentration of the target chemical species as measured by the at least one sensor with the pre-determined threshold concentration for the target chemical species and raises an alert if the difference between the two exceeds a pre-determined level.

The description for the first and second aspects of the invention also applies to the third and fourth aspects of the invention, unless the context makes clear otherwise.

The sensor as described may provide the ability to acquire large-scale, long-term average concentrations of a target chemical species. The concentration distribution information with characteristics of temporal variations (i.e. diurnal, seasonal and annual patterns) may be critical and invaluable for meaningful air, water and or soil quality and environmental impact assessments. The acquisition large-scale, long-term sample quality data using traditional analytical method can be difficult and economically unviable, because the current methods may require large-scale, long-term, continuous sampling of indefinite number of samples. In embodiments, the free ammonia concentration in a sample can be determined by Equation (6) and is the absolute average concentration at any given deployment time. This is because the determined free ammonia concentration is the result of a continuous accumulation process.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

BRIEF DESCRIPTION OF THE FIGURES

Embodiments of the invention will now be described with reference to the accompanying drawings which are not drawn to scale and which are exemplary only and in which:

FIGS. 2A and 2B show a schematic diagram illustrating the conceptual view of the $NH_3$ sensing principle.

FIG. 3C shows an exemplar original conductivity response and deployment time profiles obtained by sensor #1 from deployment solutions containing high concentrations of $\{NH_3\}_{aq}$.

FIG. 13 shows Table S1 and Table S2.

FIG. 14A shows a typical sensing system setup for laboratory experiments; FIG. 14B shows a data logger; FIG. 14C shows a self-powered data logger used for field deployment.

DETAILED DESCRIPTION OF EMBODIMENTS OF THE INVENTION

Figure 1:
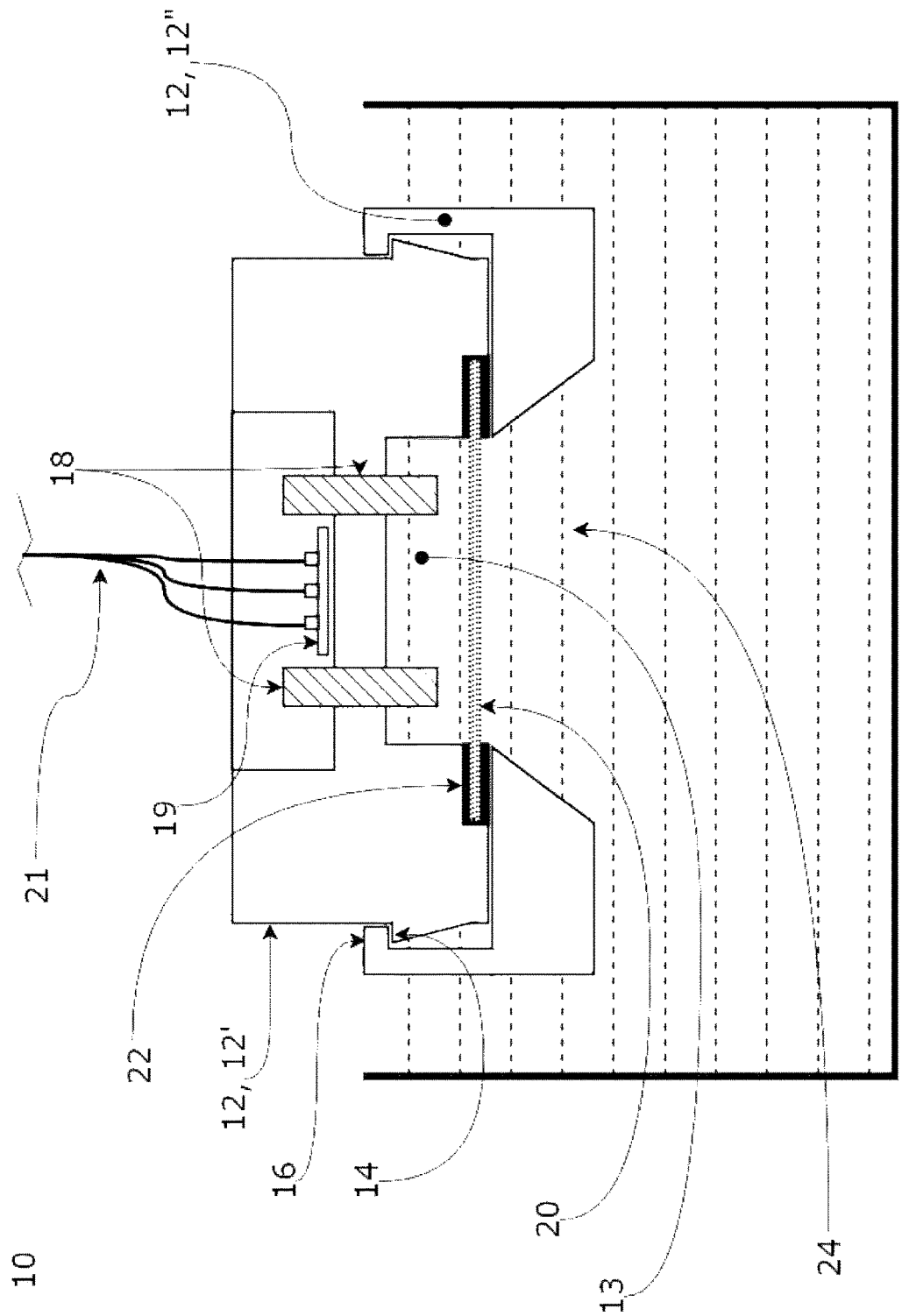
FIG. 1 shows a schematic diagram illustrating the configuration of a $NH_3$ sensor.

FIG. 1 show the configuration of a sensor 10 according to an embodiment of the present invention. The sensor 10 can be an in situ free ammonia analytical device (namely, a membrane-based conductivity sensor, MCS device). The sensor 10 comprises a housing 12.

The housing can be in two parts 12' and 12". The first part of the housing 12' can be a cylindrical base defining a reservoir in which the weak acid or weak base analytical fluid can be housed. The first part 12' can have an access via which the weak acid or weak base can be added to the reservoir 13 prior to use. The access can be an opening defining the mouth of a reservoir 13. The reservoir 13 can be filled prior to use. The reservoir 13 can be replenished with weak acid or weak base during use of the sensor. Once the weak acid or weak base has been added to the reservoir 13, the first part 12' can be sealed, so that the weak acid or weak base does not leak out of the reservoir during use. A conductivity detector 18 is arranged in the reservoir so as to be in contact with the weak acid or base in the reservoir 13. The conductivity detector 18 is connected via sensor electronics 19 and wiring 21 to an electronic device. The electronic device can be a data acquisition unit which can receive and record the conductivity data recorded by the conductivity detector 18.

The first part of the housing 12' can be sealed by reversibly engaging with the second part of the housing 12". The second part of the housing 12" can be a cap which encompasses the first part base 12'. In order to engage the first part 12' with the second part 12", the first part 12' can have a plurality of shoulders 14 arranged around the upper peripheral surface of the base 12'. The shoulders 14 can reversibly engage with complementary arms 16 extending from the second part of the housing 12". When the first and second parts 12' and 12" are mated the arms 16 can extend over and rest on the underside of the shoulders 14 to prevent or at least reduce separation of the first and second parts 12' 12" without some manual manipulation of one or the other. In an embodiment, the shoulders 14 have spaces between them, so that the second part 12' can be brought into contact with the first part 12' with the arms 16 disposed between the shoulders 14, the two parts 12', 12" can then be twisted or rotated, so that the arms 16 are rotated under the shoulder and grip onto the flange formed by the shoulders 14. In some embodiments, the first part of the housing 12' is tapered and the arms 16 are formed from a resilient material, so that the two parts 12', 12" can be forced together to interlock. When the parts 12', 12" are interlocked as shown in FIG. 1 they cannot be readily separated without some manual manipulation. Whilst the housing is shown as cylindrical, it should be understood that it can have any shape.

Prior to assembling the first and second parts 12' and 12" together, as shown in FIG. 1, the weak acid or weak base can be filled into the reservoir 13, the membrane 20 can then be arranged to cover the reservoir 13. The membrane 20 can be held in place by a gripping interference fit between the first and second parts 12', 12". In order to ensure that the weak acid or base does not leak from the reservoir 13, one or more seals 22 can be added between the first and second parts 12', 12". The seal 22 can be an annular rubber seal such as a silicon seal. The sensor can be water proof, so that it can be immersed in water without the water penetrating the reservoir.

The assembled sensor 10 has an opening 24 which allows a sample to come into contact the sampling side of the membrane 20. The sample can be aqueous or gaseous. When the sample is aqueous, the sensor can be immersed in the sample solution. When the sample is gaseous, the sensor can be placed in location in which the gas (e.g. air) can come into contact with the sensor.

In an embodiment, the sensor 10 comprises a gas permeable membrane 20, a receiving phase reservoir 13 and a 4-electrode conductivity detector 18. The sensitive 4-electrode conductivity detector can be used to detect the change in conductivity of the receiving phase solution that is directly proportional to the concentration of ammonia ($NH_3$) in the sample solution. All of these features as described are contained within a plastic housing 12. A cap 12" and two silicone spacers 22 are used to hold the membrane in place. The sensor electronics are directly immobilised on the back (base) of the plastic housing (see FIG. 1).

Analytical Principle

The sensor as shown in cross-section in FIG. 1 can allow for the real time in situ measurement of free ammonia ($NH_3$) in an aquatic, atmospheric or agricultural environment. This sensing system can in some embodiments comprise a hydrophobic gas permeable membrane 20 that is in direct contact with a boric acid ($H_3BO_3$) receiving solution of low conductivity. When the device is placed in water/air sample containing $NH_3$, $NH_3$ from the source (sample) solution transports across the semi-permeable membrane 20 and reacts with $H_3BO_3$ in the receiving solution to produce $NH_4^+$ and $H_2BO_3^-$. The produced $NH_4$ and $H_2BO_3^-$ results in an increased receiving solution conductivity, of which is directly proportional to the concentration of $NH_3$ in the sample. In such a way, the $NH_3$ concentration in the sample can be determined by the measuring the conductivity change of the receiving solution.

Without wishing to be limited by theory, the underlying principle of the invention is based on the free ammonia analytical principle. Whilst ammonia is used to underpin the principle, the skilled person will understand that the principle can apply to other chemical species that chemically react to form ionic species.

In FIG. 2B, the sampling side of the membrane 20 is shown on the right-hand side of the graph in FIG. 2B. In the embodiment shown, the sample is an aqueous sample solution. The analytical side of the membrane is shown on the left-hand side of the graph in FIG. 2B. In the embodiment shown, there is a weak acid on the analytical side, the weak acid comprises hydrogen borate ($H_3BO_3$). Free ammonia (NH) present in the sample solution will transport across the gas permeable membrane. The permeated $NH_3$ stoichiometrically reacts with boric acid ($H_3BO_3$) at the inner membrane/solution interface at the analytical side to produce $NH_4^+$ and $H_2BO_3^-$ (Equation (1)). The reaction between $NH_3$ and boric acid leads to an increase in conductivity at the analytical side of the membrane, the increase in conductivity is directly proportional to the ammonium ($NH_4^+$) concentration in the reactive receiving solution (phase) at the analytical side of the membrane.

A typical sensor in one embodiment consists of three essential elements: a gas permeable membrane (GPM), an EC detector and a boric acid ($H_3BO_3$) receiving phase. As illustrated in FIG. 2A, when a sensor is deployed in an aquatic sample, the dissolved ammonia ($\{NH_3\}_{aq}$) will diffuse to the outer GPM interface, convert into gas phase ammonia ($\{NH_3\}_g$) at the interface via evaporation and permeate into GPM. The permeated $\{NH_3\}_g$ inside the GPM will rapidly diffuse to the inner surface, where $\{NH_3\}_g$ will instantaneously and stoichiometrically react with $H_3BO_3$ at the inner GPM interface to produce $NH_4^+$ and $H_2BO_3^-$ in the receiving phase (Equation (1)). In effect, the rapidity of this acid-base reaction can efficiently reduce and maintain the concentration of $\{NH_3\}_g$ at the inner GPM surface to essentially zero ($[NH_3]_R \approx 0$), continuously driving ammonia transport across the GPM.

$$NH_3 + H_3BO_3 \rightarrow NH_4^+ + H_2BO_3^- \qquad (1)$$

Considering that ammonia concentrations of most aquatic environments are low ($\mu g\ L^{-1}$-$mg\ L^{-1}$) and the sensing is operated under ambient environmental temperatures, also considering that the $\{NH_3\}_g$ ammonia diffuses inside GPM and reacts with boric acid at the inner GPM interface are rapid, it is reasonable to assume that the conversion of $\{NH_3\}_{aq}$ into $\{NH_3\}_g$ at the outer GPM interface is the rate limiting step of the membrane process. Because this conversion process is a continuous dynamic evaporation process, and for a given GPM, temperature and deployment time, the rate of $\{NH_3\}_g$ evaporation is directly proportional to $\{NH_3\}_{aq}$ concentration in a sample ($[NH_3]_{Sample}$), therefore, the flux of ammonia (J) permeating through GPM can be given as:

$$J = \frac{d([NH_3]_g)}{dt} = k[NH_3]_{Sample} \qquad (2)$$

As the permeated $NH_3$ from sample is stoichiometrically converted into ammonium ($NH_4^+$) via the interfacial reaction (Equation (1)), the rate of $NH_4^+$ concentration increase in the receiving phase can therefore be expressed as:

$$\frac{d([NH_4^+]_R)}{dt} = \frac{J}{V_R} = \frac{k}{V_R}[NH_3]_{Sample} \qquad (3)$$

Where, $[NH_4^+]_R$ is the accumulated $NH_4^+$ concentration in the receiving phase and $V_R$ is the volume of the boric acid receiving phase. Because the conductivity of the receiving phase is directly promotional to $[NH_4^+]_R$, therefore, the rate of the receiving phase conductivity increase ($R_{CI}$) can be presented as:

$$R_{CI} = \frac{d\sigma}{dt} = \rho\frac{d([NH_4^+]_R)}{dt} = \rho\frac{k}{V_R}[NH_3]_{Sample} = K[NH_3]_{Sample}. \qquad (4)$$

Where, $\rho$ is the proportional constant of EC detector. K depends on the property and exposed area of GPM, the boric acid receiving phase volume, characteristics of EC detector and the deployment temperature. For a given sensor with temperature correction, K is a constant and can be readily experimentally determined. That is, the instantaneous ammonia concentration can be determined by simply measuring the $R_{CI}$ of the receiving phase. It is important to note that because K is a sensor specific constant, therefore, once K value of a sensor is determined, no ongoing calibration may be required during deployment. This is a distinctive advantage for a field-based analytical technique as it will not only reduce the maintenance and operational costs but also in some embodiments will increase the reliability.

An ability to determine average pollutant concentration over a long time period can provide useful information for environmental evaluation and impact prediction. However, for most analytical techniques, it is impractical to determine average concentration over a prolonged period because it requires very high sampling frequency, resulting in a huge number of samples, hence, a huge assay task and associated cost. In some embodiments, the sensor can accumulate the data gathered during deployment to determine the average concentration of a target chemical species. For a given deployment time (t), Equation (4) can be rewritten as:

$$d\sigma = \rho \cdot d([NH_4^+]_R) = K\int_0^t ([NH_3]_{Sample})dt \qquad (5)$$

According to Equation (5), the average ammonia concentration ($\overline{[NH_3]}_{Sample}$) over a deployment period of t can be determined by:

$$\overline{[NH_3]}_{Sample} = \frac{d\sigma}{Kt} \qquad (6a)$$

Where, dσ is the total conductivity increment of the receiving phase over the deployment period. It should be noted that $\overline{[NH_3]}_{Sample}$ is an absolute average concentration because the accumulated $[NH_4^+]_R$ in the receiving phase is the result of the integration of instantaneous sample ammonia concentrations ($\int_0^t ([NH_3]_{Sample})dt$) over the entire deployment period. For a deployment solution containing a fixed concentration of $\{NH_3\}_{aq}$, Equation (6a) can be rewritten as:

$$[NH_3]_{Sample} = \frac{R_{CI}}{K} \qquad (6b)$$

It is well known that $NH_3$ and $NH_4^+$ always coexist in aquatic environment. For a given temperature, assuming $NH_3$ and $NH_4^+$ are in an equilibrium state, then $NH_4^+$ concentration in the sample ($[NH_4^+]_{Sample}$) can be calculated from the determined $[NH_3]_{Sample}$ (Equation (7)).

$$[NH_4^+]_{Sample} = \frac{K_b}{[OH^-]} \times [NH_3]_{Sample} \qquad (7)$$

Where, $K_b$ is the base constant of ammonia dissociation.

The described analytical principle should possess high accuracy. Any measurement errors are more likely contributed by the temperature effect on $D_M$ and σ measurement, which can be precisely corrected in real-time by temperature data obtained from the additional temperature probe. The sensor device may therefore be cheap to build, have low operational coasts, be reusable, and in some embodiment is easy to maintain and use. The device may be readily produced on a mass scale.

Some other detectors rely on the micro-distillation flow injection ammonia detection system, where the ammonia containing sample needs to be pumped into a micro-boiler and mixed with NaOH to extract ammonia from the sample, and the extracted ammonia needs to be condensed and adsorbed before detection. In the present sensor, however, the sensor can directly and continuously extract ammonia from sample through the gas-permeable membrane. The process is driven by a simple neutralization reaction of ammonia with boric acid, and which simultaneously realizes the detection of the ammonia. It is this unique feature of sensor that may make in situ real-time ammonia monitoring possible.

In the following examples of various embodiments of the invention, the analytical principles that enables the sensor to continuously monitor instantaneous ammonia concentrations and to determine the average ammonia concentration over a given deployed period are proposed and experimentally validated. A pre-calibration strategy is also developed to eliminate the need for ongoing calibration for better practicality and minimized operational and maintenance costs. The performance of the developed sensor was evaluated with synthetic samples and field deployments.

EXAMPLES

Embodiments of the invention will now be described with reference to the following examples which are not limiting.
1.1 Chemicals, Solutions and Sample Analysis.

All chemicals used in this work were of AR grade and purchased from Merck. All solutions were prepared using deionised water (Millipore Corp., 18MΩ cm). Sodium hydroxide was used to adjust testing solution pH. Unless otherwise stated, the receiving phase used in this work was about 0.500 mole $L^{-1}$ boric acid.

The ammoniacal nitrogen ($NH_3$—N) is determined by APHA Standard Method, where needed, the standard distillation method was used to achieve sample pre-concentration.
1.2 Apparatus and Methods.

An exemplary two-compartment cell is shown in FIG. 1 and FIGS. 2A and 2B. The cell containing about 85.0 mL of about 0.010 M HCl and NaCl solutions separated by a PTFE gas-permeable membrane with an exposed area of 1.8 cm² was used to investigate the transport of H⁺ across the PTFE membrane. A pH electrode was used to monitor pH change of NaCl solution.

FIG. 1 shows the assembly of the sensor. The base comprises a receiving phase reservoir and a 4-electrode conductivity detector (EC detector). The EC detector was constructed by directly inserting 4 stainless steel rods (1.5 mm in diameter) into the base with the control electronic circuit board being directly mounted onto the back of the base and fully sealed for waterproof. To minimise electromagnetic interferences, the analogue signal generated by EC detector is in situ converted into digital signal by the control electronics shown in FIG. 1. A PTFE membrane purchased from Merck (Fluoropore™, pore size: about 0.22 μm, porosity: about 85%, diameter: about 47 mm, thickness: about 150 μm) was employed as the gas permeable membrane. The sensor was assembled by filling the receiving phase reservoir with about 2.00 mL of about 0.500 mole $L^{-1}$ of boric acid solution and clipping the cap onto the base with a PTFE membrane and silicone spacers in between. The exposed PTFE membrane area is about 7.07 cm².

FIG. 14 FIGS. 14A-14C show a typical sensing system setup for laboratory experiments. Other than the sensors themselves, the system comprises a data logger (FIG. 14B), a wireless data receiver, a control computer and a sample tank. Each data logger can host up to 8 sensors (including temperature and pH sensors). A computer, through the wireless data receiver communicates with the data logger for data transfer/storage and operational control. The control software has an automatic temperature and pH correction function. Two sample tanks with capacities to hold about 4 and about 25 L of sample solutions were employed in this work. Unless otherwise stated, for all experiments, a temperature sensor and a pH sensor are deployed together with sensors.

1.3 Validation of the Principle

All validation experiments were carried out using sensors shown in FIG. 1 under a constant temperature of about 25° C., unless otherwise stated. For all experiments, a temperature sensor and a pH sensor were deployed together with sensors. The sensor used for these experiments, K (25° C.)=1.35×10⁻³ µS cm⁻¹ min⁻¹ µg⁻¹ L (denoted as sensor #1).

Figure 3A:
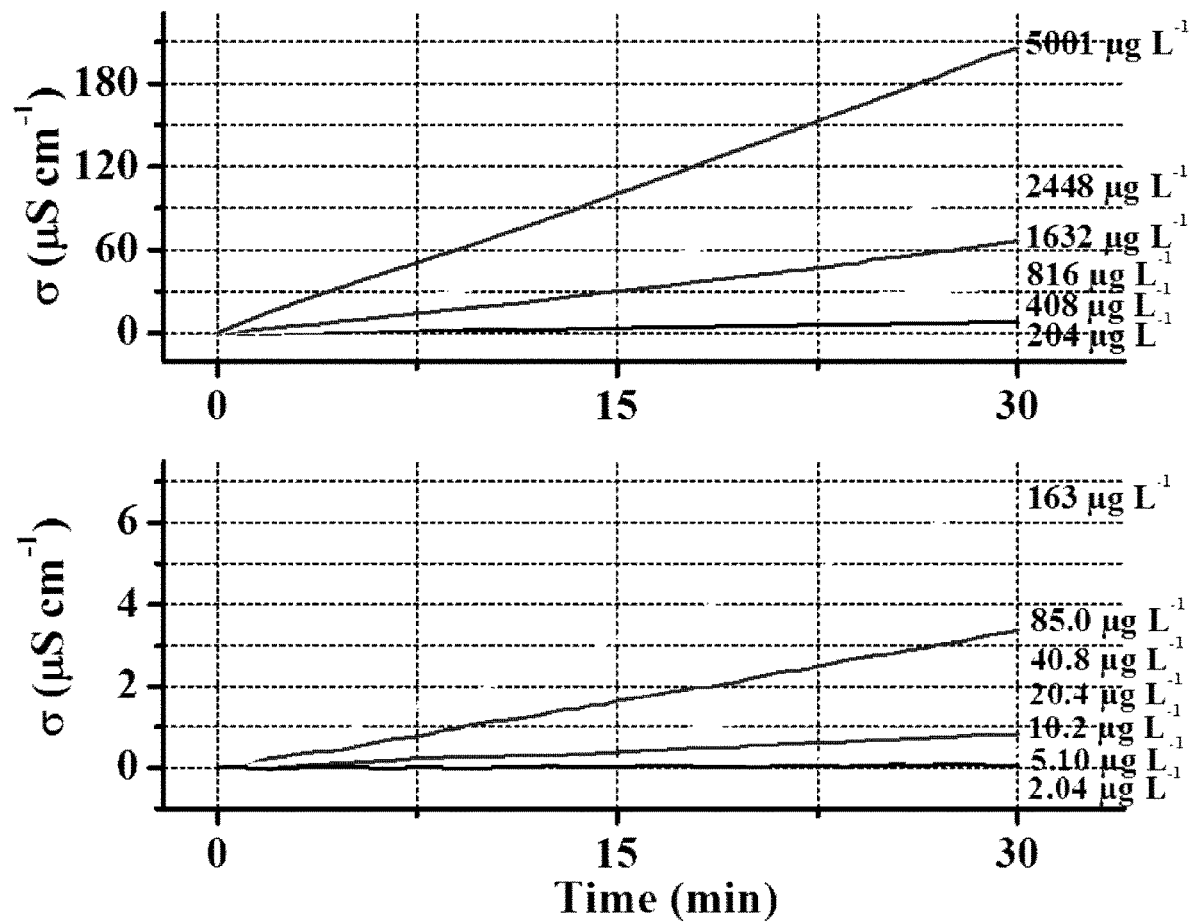
FIG. 3A shows an exemplar original conductivity response and deployment time profiles obtained by sensor #1 from deployment solutions containing different concentrations of $NH_3$.
Figure 3B:
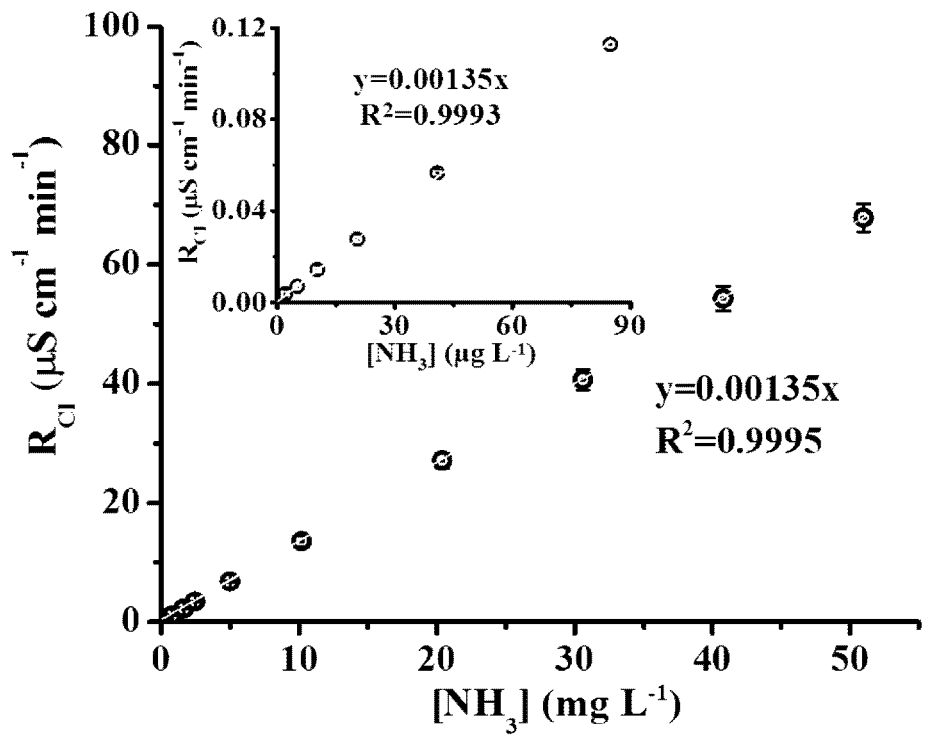
FIG. 3B shows an exemplar $R_{Cl}$—[$NH_3$] relationship derived from FIGS. 3A and 3D.

For all σ-t curves reported, the conductivity data was recorded at 1 reading per minute frequency. FIGS. 3A and 3D shows 3 sets of original sensor conductivity response (σ)-deployment time (t) profiles obtained from different $\{NH_3\}_{aq}$ concentrations ranged from about 2 µg L⁻¹ to about 50 mg L⁻¹. Perfect linear curves were observed for all cases investigated. For each $[NH_3]_{Sample}$, $R_{CI}$ can be derived from the slope of the corresponding σ-t curve. For a given sensor and temperature, according to Equation (4), $R_{CI}$ should be directly proportional to $[NH_3]_{Sample}$. FIG. 3B shows a plot of $R_{CI}$ against $[NH_3]_{Sample}$. As predicted by Equation (4), a linear relationship can be obtained over the entire $\{NH_3\}_{aq}$ concentration range investigated. It is important to note that the sensor constant (K) equals the slope value of the $R_{CI}$—$[NH_3]_{Sample}$ curve.

Figure 3C:
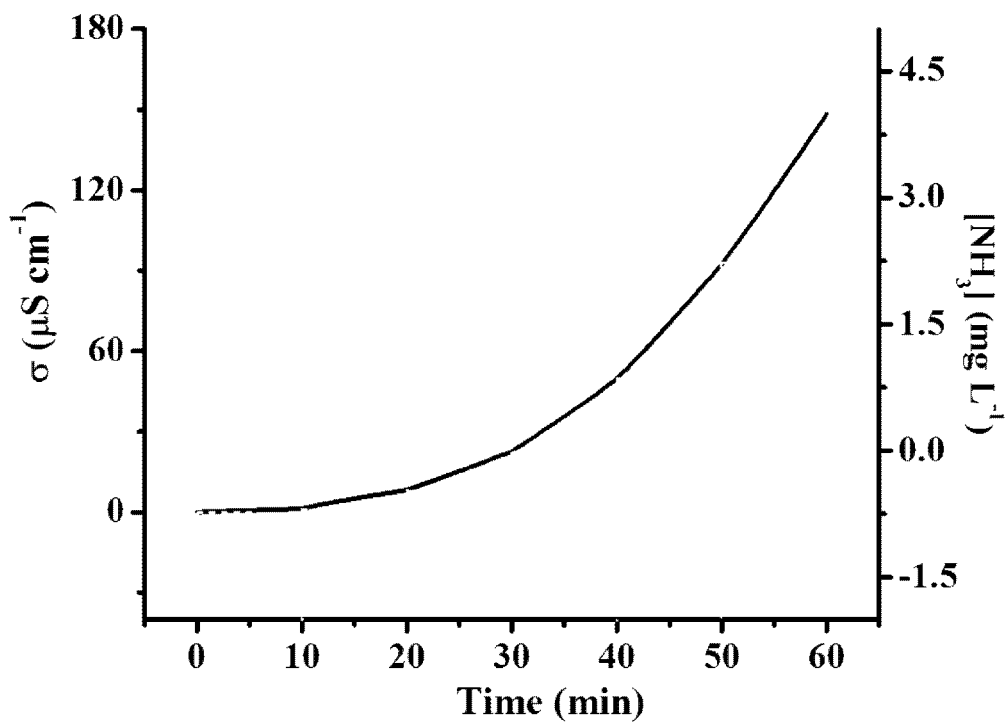
FIG. 3C shows an exemplar conductivity response obtained from a deployment solution with successively increased $NH_3$ concentrations and corresponding $\overline{[NH_3]}_{Sample}$ ((blue lines) determined by Equation (6b)
Figure 3D:
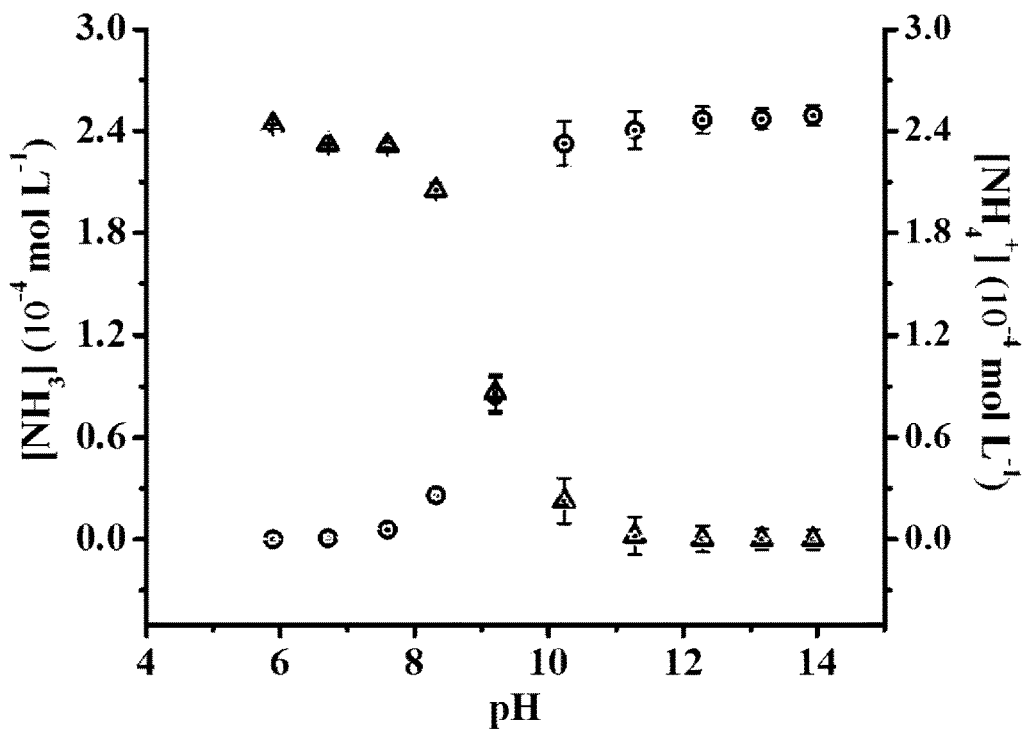
FIG. 3D shows the determined concentrations, $[NH_3]_{Sample}$ (o) and $[NH_4^+]_{Sample}$ (△), by Equations 4 and 7, from a synthetic freshwater deployment solution containing about 0.240 µmol $L^{-1}$ of $NH_4Cl$ with different pHs.
Figure 3E:
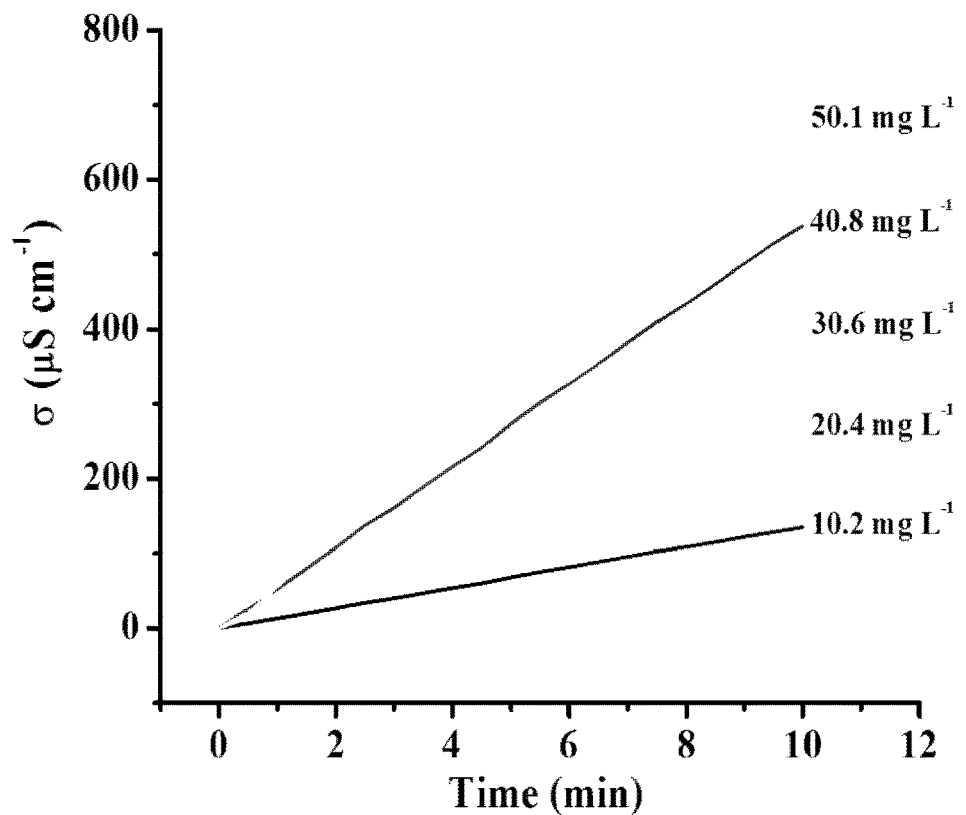

Sensor #1 was used to obtain a set of conductivity responses from a synthetic freshwater deployment solution with successively increased $NH_3$ concentrations (FIG. 3C). The blue lines shown in FIG. 3C are corresponding $\overline{[NH_3]}_{Sample}$ determined by Equation (6b). Table S1 in FIG. 13 summarizes the measured $R_{CI}$ for each investigated $\{NH_3\}_{aq}$ concentration derived from FIG. 3C and the determined $\overline{[NH_3]}_{Sample}$ according to Equation (6b). If Equation (6b) is correct, the determined $\overline{[NH_3]}_{Sample}$ should equal to the added ammonia concentration. The results show that for all cases investigated, the deviations between the determined $\overline{[NH_3]}_{Sample}$ and added ammonia concentration are less than ±5%, signifying the validity of Equation (6) for determining absolute average concentration of $\{NH_3\}_{aq}$ over a given deployment period.

1.4 Further Validation of the Analytical Principle

A set of experiments was carried out to validate Equation (7). For all experiments, a 25 L of synthetic freshwater solution containing about 0.240 µmol L⁻¹ of $NH_4Cl$ was adjusted to different pHs between about 5.90 and about 13.94, and used as deployment solutions.

Figure 6:
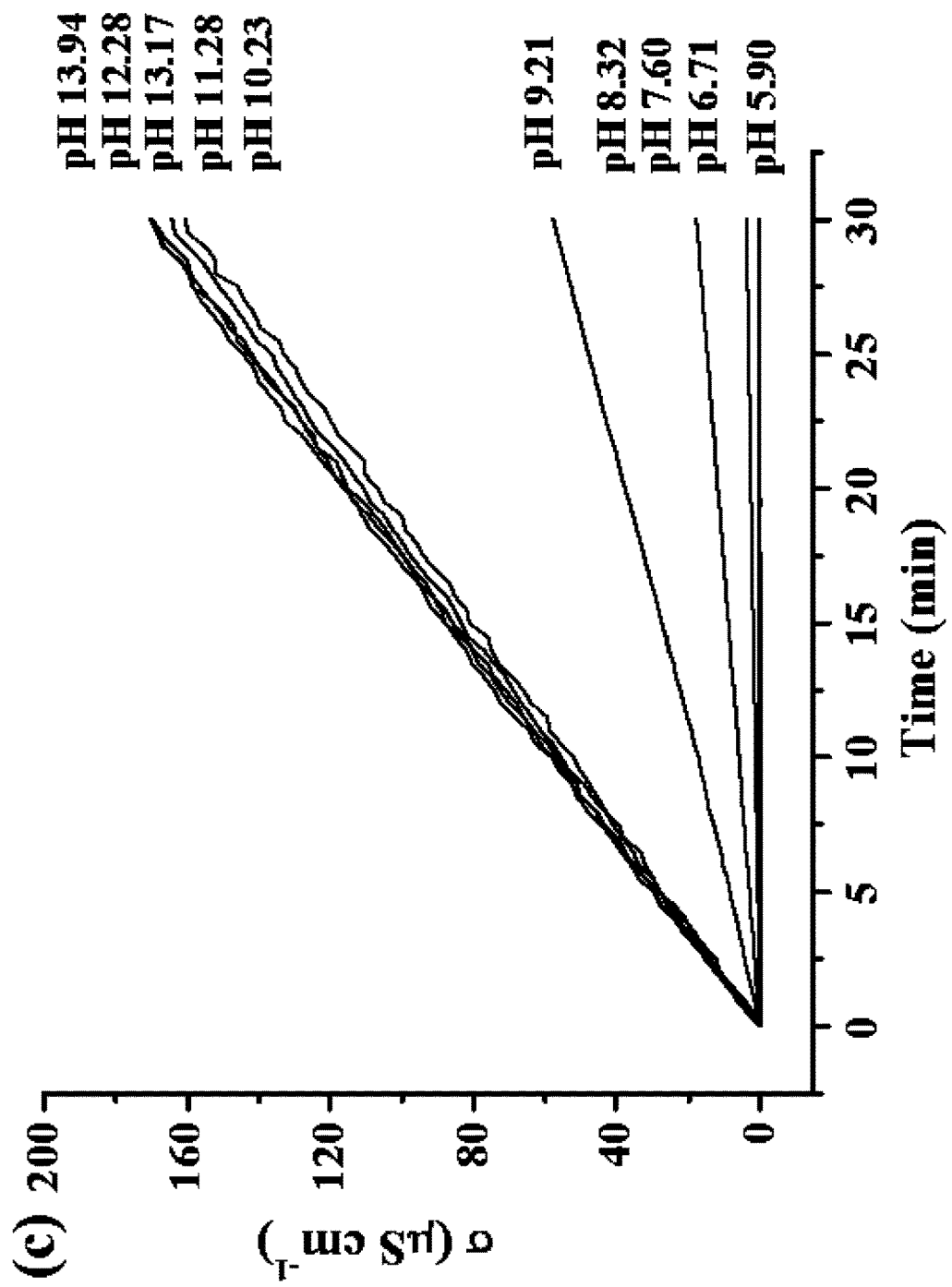
FIG. 6 shows σ-t plots obtained from a simulated freshwater deployment solutions containing about 0.240 µmol $L^{-1}$ of $NH_4Cl$ with different pHs.

FIG. 6 shows the recorded σ-t curves from deployment solutions with different pHs. $[NH_3]_{Sample}$ of deployment solutions with different pHs were determined by Equation (4) and used to calculate the corresponding $[NH_4^+]_{Sample}$ in accordance with Equation (7).

FIG. 3D shows the plots of both $[NH_3]_{Sample}$ and $[NH_4^+]_{Sample}$ against pH, and theoretical distributions of $[NH_3]$ and $[NH_4^+]$ with pH. It should be noted that $K_b$ (25° C.)=1.75×10⁻⁵ was used for all calculations. It can be seen that the determined $[NH_3]_{Sample}$ and $[NH_4^+]_{Sample}$ agree with theoretical values within pH range of about 5.90 to about 13.94. Considering that the pH range of aquatic environments is normally between about 6 and about 9, the results shown in FIG. 3D confirm that Equation (7) is applicable for determination of $[NH_4^+]$ of aquatic environments. In fact, $[NH_3]$ and $[NH_4^+]$ of aquatic environments can be simultaneously monitored by Equations (4) and (7), respectively. Furthermore, the absolute ammonium concentration over a given deployment period ($\overline{[NH_4^+]}_{Sample}$) can be obtained based on the determined $\overline{[NH_3]}_{Sample}$ in accordance with Equation (6).

The results shown in FIG. 3A suggest that sensor is capable of directly determining about 2 µg L⁻¹ of free ammonia. In fact, the sensitivity can be further increased by simply extending the deployment time because sensor is an accumulative method. Also, FIG. 3B shows an upper linear range of about 50 mg L⁻¹, which can be readily extended by reducing deployment time. Furthermore, the sensitivity, linear range and maximum deployment time can be tuned by altering sensor design. A sensor with a higher ratio of exposed membrane area to boric acid receiving phase volume will possess higher sensitivity but lower upper linear range and shorter maximum deployment time.

Figure 7:
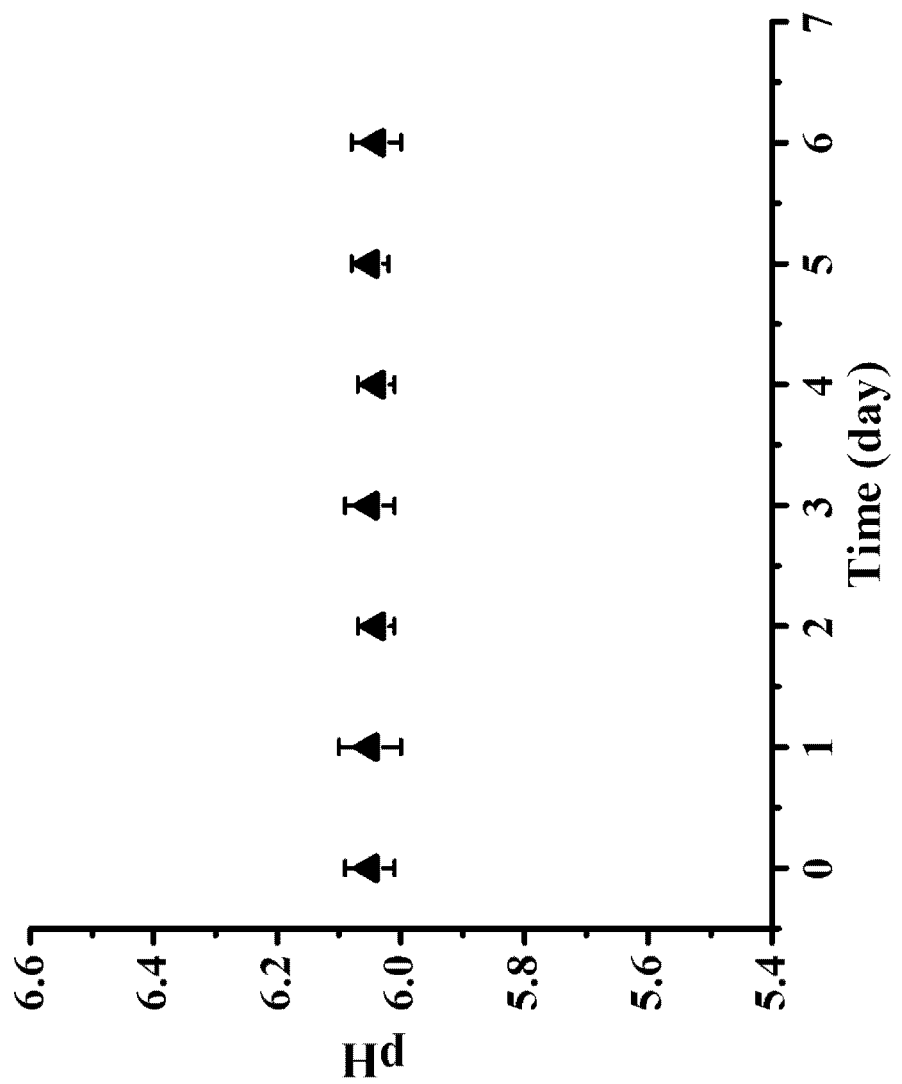
FIG. 7 shows the measured NaCl compartment pH against time.

The selectivity is an important performance indicator of many analytical applications, especially for field-based environmental monitoring application, where the sample matrixes can be highly diversified and complex. The selectivity of the sensor is therefore investigated. $H^+$ was selected as the probing ion because it is the smallest ion in any aqueous media. The transport of $H^+$ across the PTFE membrane was investigated using a two-compartment cell (FIG. 1) with about 0.01M HCl and NaCl solutions separated by a PTFE gas-permeable membrane. FIG. 7 shows a typical pH-time profile of NaCl solution. No measurable pH decrease trend can be observed over the test period of 5 days, which means that the transport of $H^+$ across the membrane did not occur during the test period. This also means that no any ionic species could permeate through the PTFE membrane.

Figure 8B:
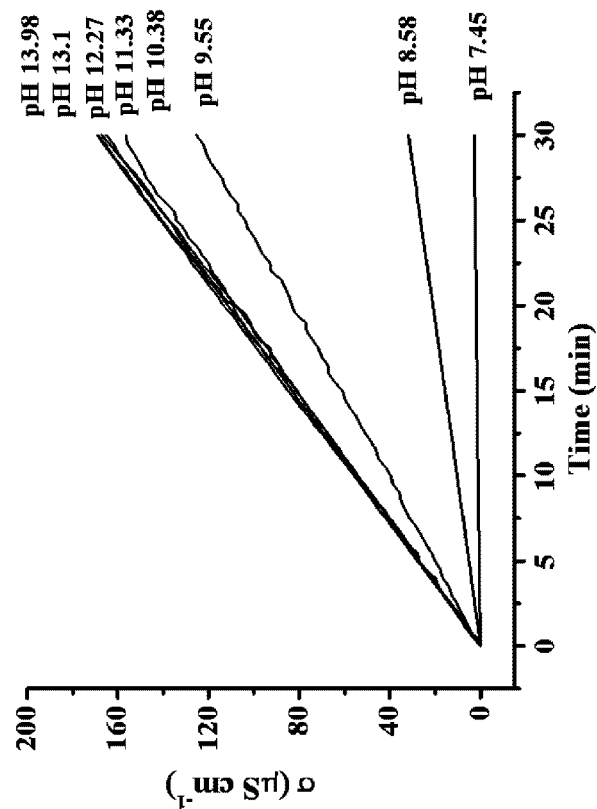
FIG. 8B shows measured $NH_3$ concentrations (circle points) by Equation (4) using $R_{Cl}$ data derived from (a) and corresponding $NH_4^+$ concentration (triangle circle points) determined by Equation (7).
Figure 8A:
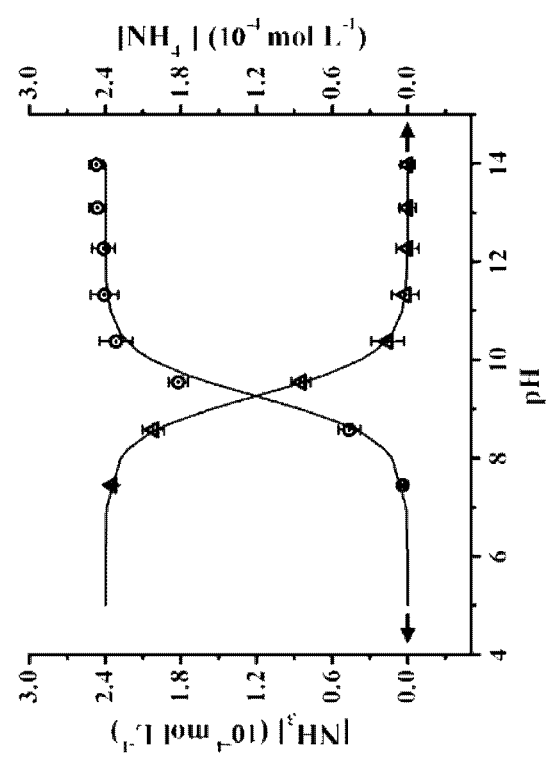
FIG. 8A shows σ-t plots obtained from a simulated seawater deployment solutions containing about 0.240 µmol $L^{-1}$ of $NH_4Cl$ with different pHs.
Figure 9A:
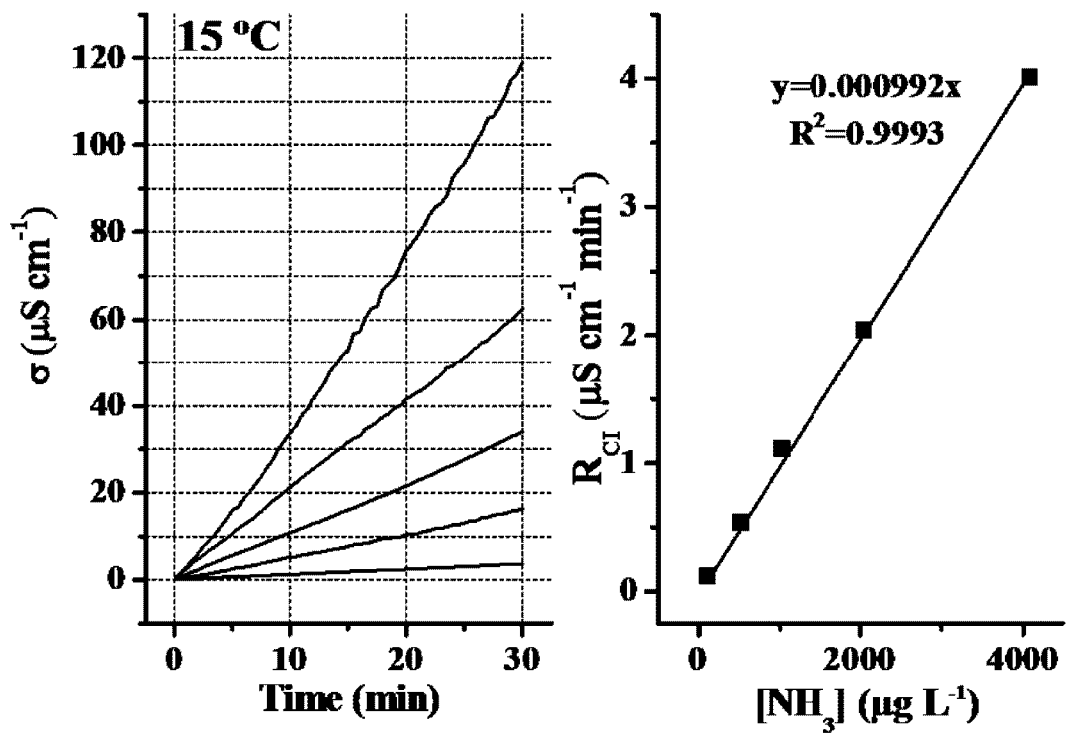
FIG. 9A to 9F show typical σ-t and corresponding $R_{Cl}$—$[NH_3]$ curves determined by sensor #1 from a set of deployment solutions containing about 102, about 510, about 1020, about 2040, about 4080 µg $L^{-1}$ of $NH_3$ with different temperatures.
Figure 9B:
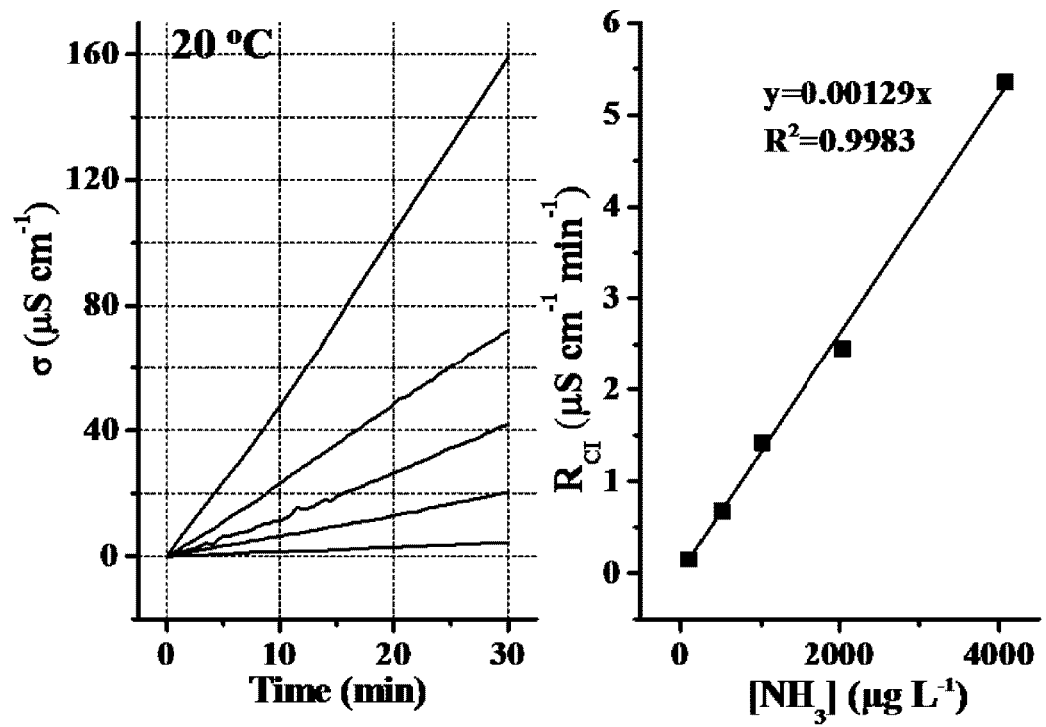
Figure 9C:
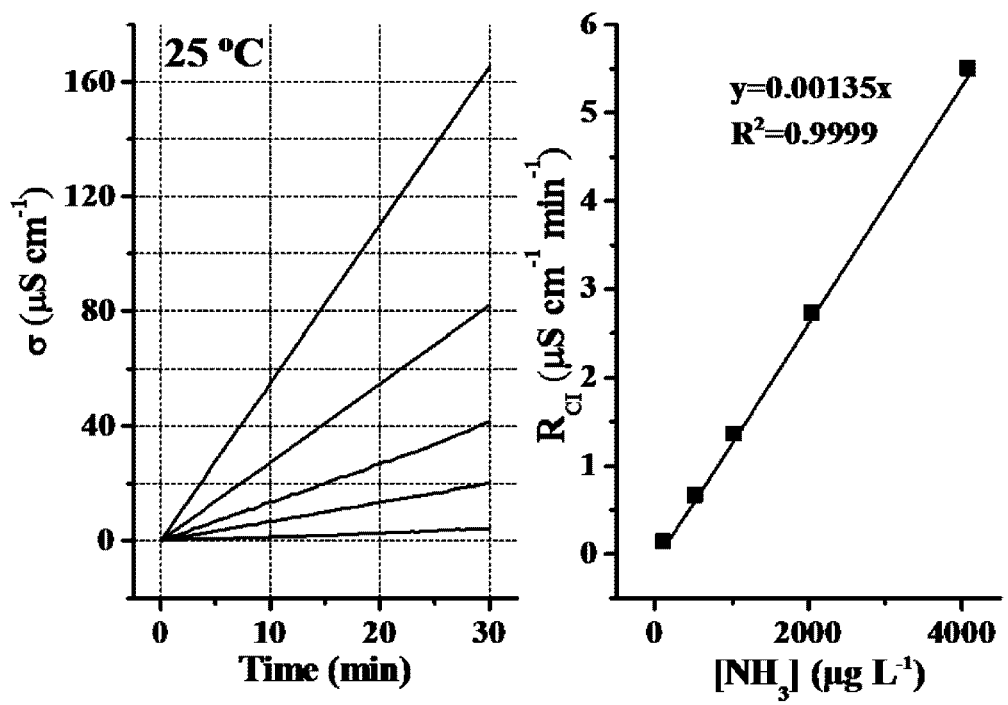
Figure 9D:
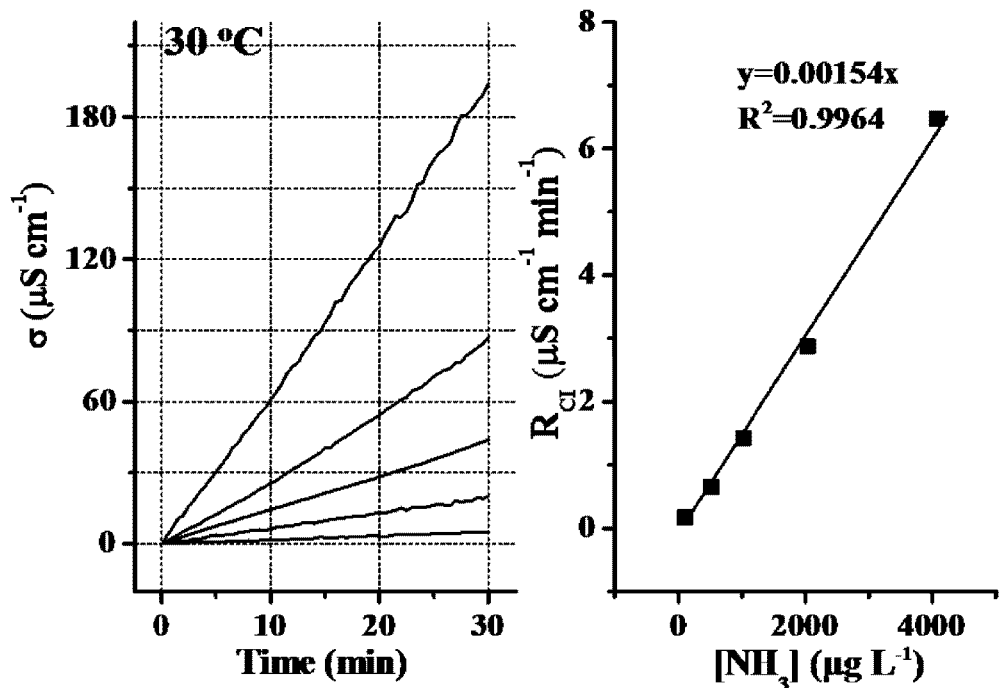
Figure 9E:
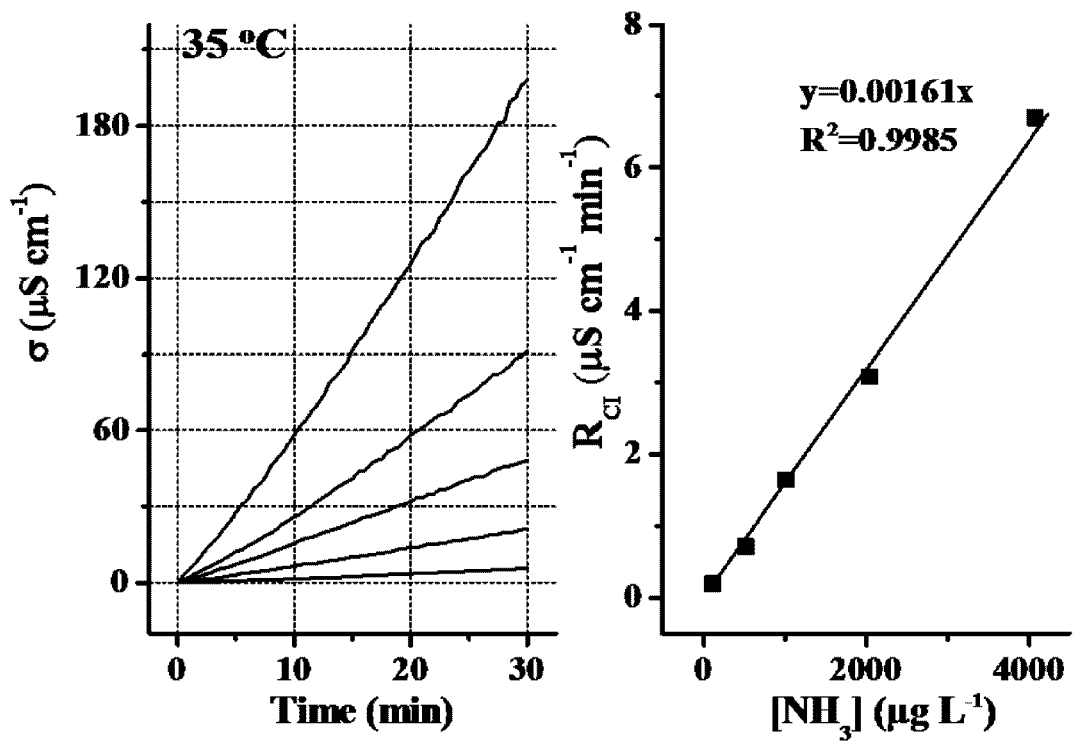
Figure 9F:
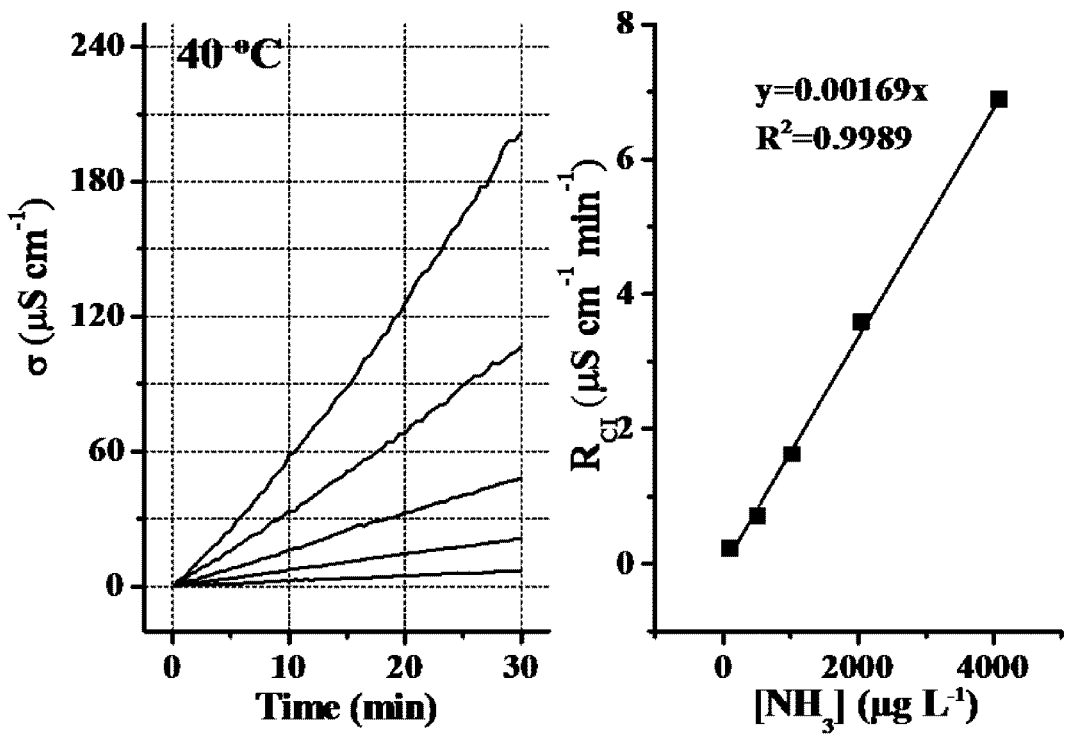

This may not be a surprising outcome when considering the hydrophobic nature of the PTFE membrane. Based on acid-base properties, dissolvable gases in aquatic environments can be classified into neutral (i.e., $O_2$, $N_2$, etc.), acidic (i.e., $CO_2$, $H_2S$, $SO_2$, etc.) and basic (i.e. $NH_3$) gases. According to the sensor sensing principle (FIG. 2B), only basic gases can continuously permeate through the membrane driven by the acid-base reaction at the inner membrane interface, while neutral and acidic gases cannot because they are not reactive with boric acid. To the best of the inventor's knowledge, ammonia is the only dissolvable basic gas in aquatic environment with appreciable solubility. Hence, the present sensor can be considered specific for ammonia detection, regardless the type of aquatic environments, as demonstrated by FIGS. 8A and 8B where the determined $[NH_3]_{Sample}$ and $[NH_4^+]_{Sample}$ in synthetic seawater matrix within a wide pH rage are almost identical to those obtained from freshwater matrix (FIG. 3D).

1.5 Sensor Calibration

An analytical technique that requires no ongoing calibration is highly desirable for field-based environmental monitoring applications. According to Equation (4), K is a sensor specific constant. For sensor #1, the constant at about 25° C. was determined as K(25° C.)=1.35×10⁻³ µS cm⁻¹ min⁻¹ µg⁻¹ L (FIG. 3B). However, for a given sensor, K is also dependent on temperature, which needs to be corrected for practical use. A two-step correction strategy was therefore developed for sensor calibration: (i) correcting the temperature effect on EC detector of the sensor to normalise all measured conductivity under different temperatures (or) to the 'standard' conductivity value at about 25° C. ($\sigma_{25}$); (ii) using $\sigma_{25}$ data to obtain the K-temperature dependent relationship of the sensor and determine K (T) for practical use.

Figures 4A, 4B:
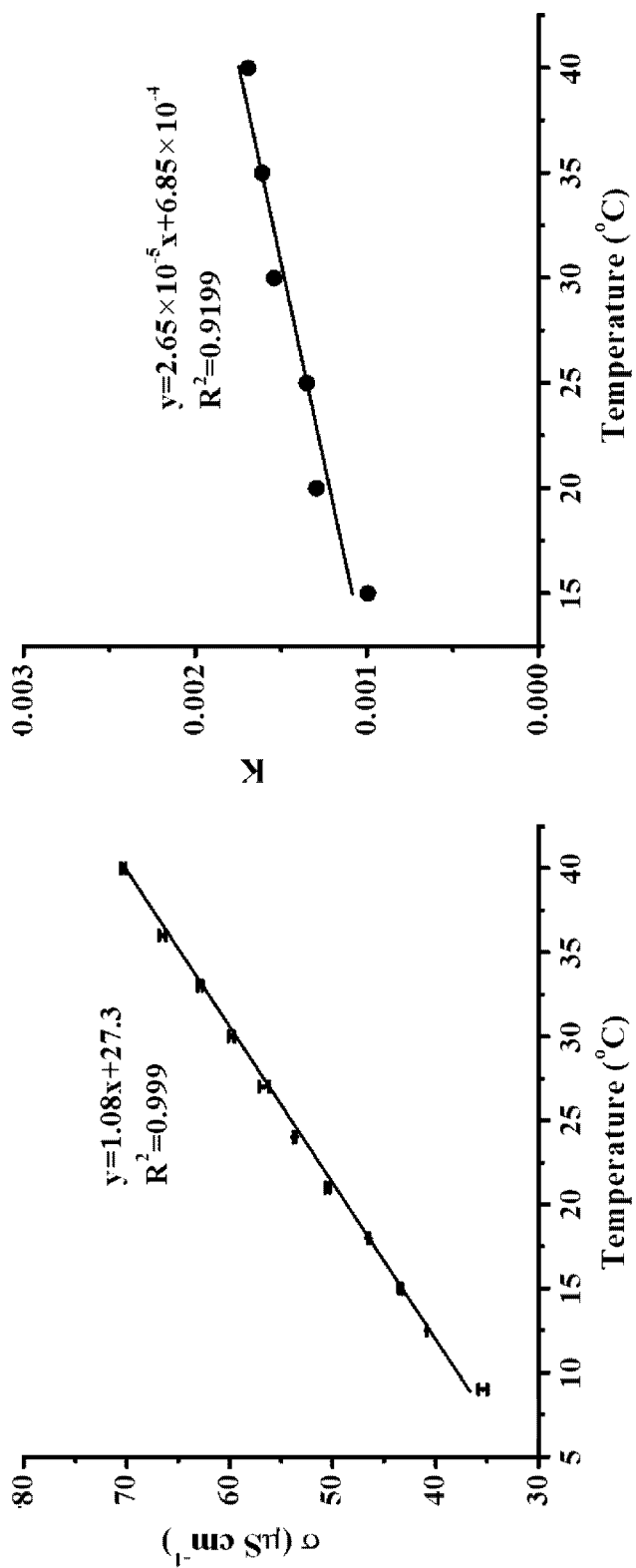
FIG. 4A shows a temperature correction curve for the EC detector in sensor #1.
FIG. 4B shows a temperature correction curve for sensor #1 constant.

FIG. 4A shows the plots of measured conductivity changes of with temperature by sensor #1 from about 0.500 mole L$^{-1}$ boric acid receiving phase. The slope and intercept values of about 1.08 µs cm$^{-1}$° C.$^{-1}$ and about 27.3 µs cm$^{-1}$ may be respectively obtained. Therefore, the measured $\sigma_T$ under temperature (T, ° C.) by the EC detector in sensor #1 may be converted to $\sigma_{25}$ by:

$$\sigma_{25}=\sigma_T+1.08\times(25-T) \quad (8)$$

It should be noted that Equation (8) is sensor specific and may only be used to correct EC detector for sensor #1. In practice, a temperature correction formula for each sensor needs to be determined. For this work, the all measured a values are real-time corrected to $\sigma_{25}$ values by the sensor control software based on the measured temperature and the predetermined EC detector temperature correction formula (like Equation (8)) of the sensor. As such, all conductivity values reported in this work are of $\sigma_{25}$ values, unless otherwise stated.

FIGS. 9A-9F shows six groups of typical σ-t and corresponding $R_{CI}$—[NH$_3$] curves determined by sensor #1 from a set of deployment solutions containing different concentrations of NH$_3$ and with different temperatures between about 15° C. and about 40° C. Each group of σ-t curves is measured under a constant temperature which was used to obtain $R_{CI}$ values for determination of the constant (K(T)) under the corresponding temperature. The constant and temperature dependent relationship can then be determined from the K(T)-T curve shown in FIG. 4B:

$$K(T)=2.65\times10^{-5}T(° C.)+6.85\times10^{-4} \quad (9)$$

Equation (9) is sensor specific and can only be used to correct the temperature induced constant changes for sensor #1. In practice, each sensor needs to be calibrated to obtain its temperature correction equation. Again, the sensor control software will automatically correct the temperature effect.

Figure 10:
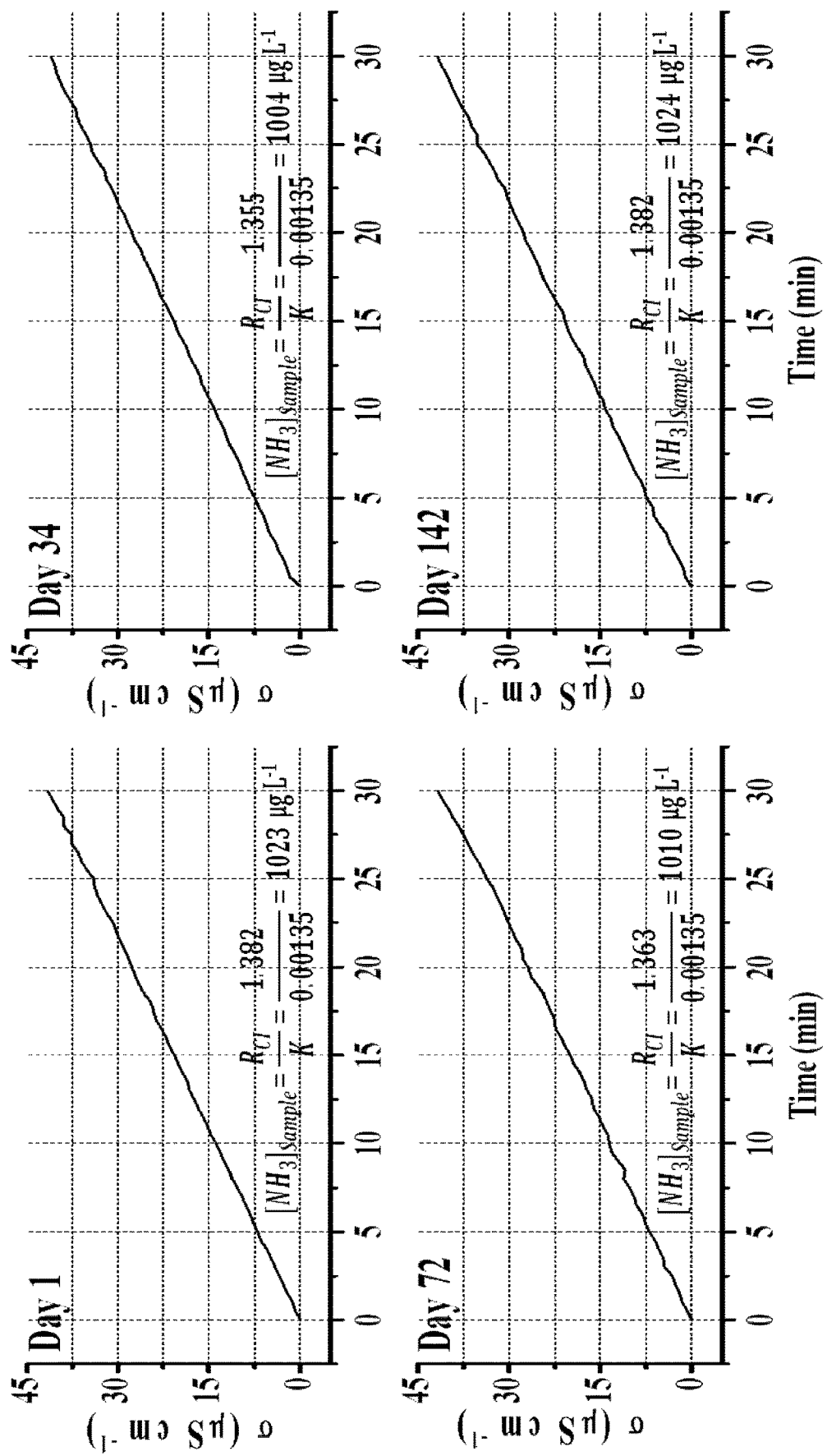
FIG. 10 shows σ-t curves obtained by sensor #1 over a period of 142 days from a deployment solution containing about 1020 µg $L^{-1}$ of added $NH_3$.

As aforementioned, in theory, once a sensor is calibrated, the obtained constant should not change with time, therefore, no ongoing calibration is needed. FIG. 10 shows a set of σ-t curves obtained by sensor #1 over a period of 142 days from a deployment solution containing about 1020 µg L$^{-1}$ of added NH$_3$. Over the entire testing period, other than obtaining the results shown in FIG. 10, the same sensor was also used for various other experiments without calibration. The determined $\overline{[NH_3]}_{Sample}$ values with the constant shown in Equations (8) and (9) are almost identical to those added NH$_3$ concentrations, demonstrating that a calibrated sensor can be used over a prolonged period without the need for calibration. Other sensors (Table S2 of FIG. 13) used in this work were calibrated in the same way as described above.

1.6 Field Deployment

Figure 15B:
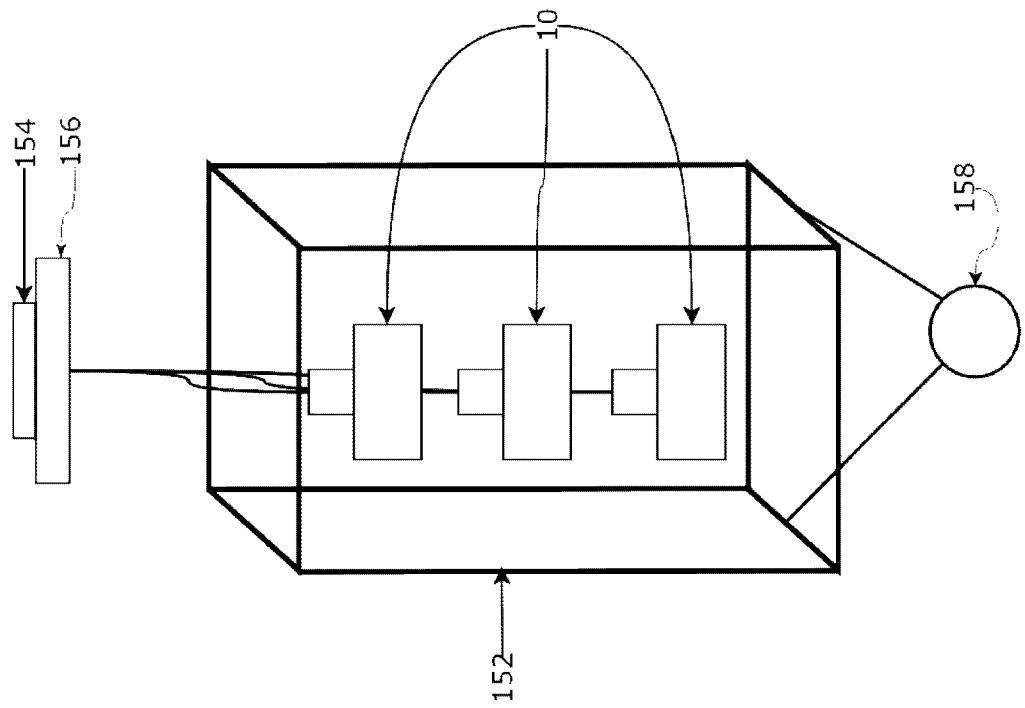
FIGS. 15A and 15B show schematic diagrams illustrating: (a) planar (horizontal) and (b) a vertical field deployment approaches of the device.
Figure 15A:
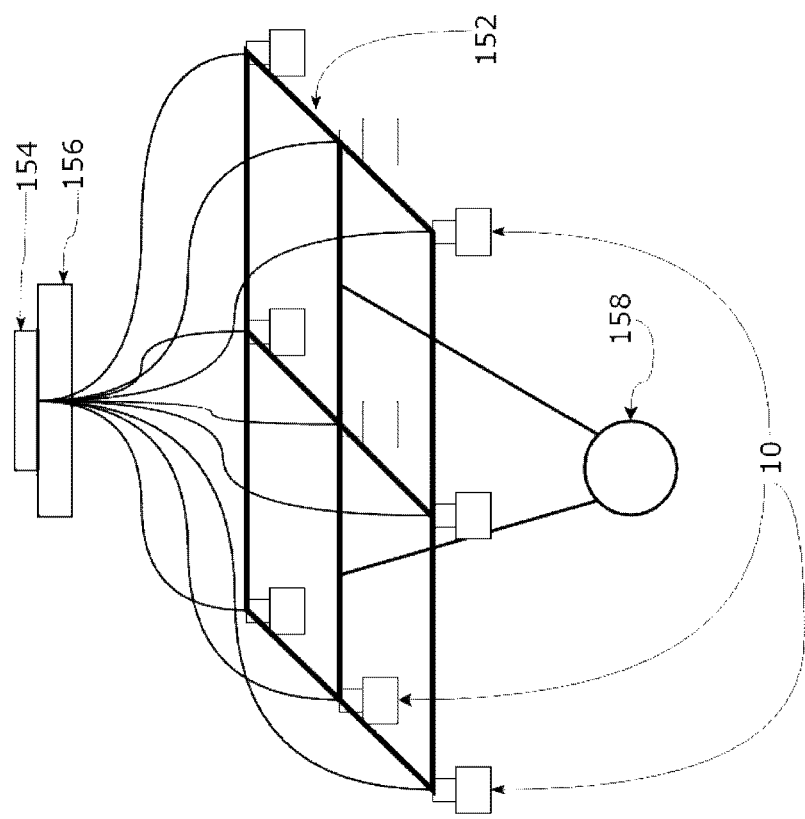

All field deployments were carried out using a self-powered data logger (FIG. 14A) that can hold 6 sensors, 1 temperature sensor and 1 pH sensor to continuously operate up to 30 days. The data logger is remotely controlled by a computer. FIGS. 15A and 15B illustrates the field deployment of sensors 10, mounted to two different embodiments of a device holder 152. The data acquisition/communication unit 154, connected to each of the sensors 10, is depicted in FIGS. 15A and 15B as mounted to a Floater 156. The field deployment means may further comprise an anchor 158 to anchor the field deployed sensors in position. The recorded temperature and pH data are used for data corrections. For this work, sensors were deployed at sites in Gold Cost City, Queensland State of Australia.

Sites #1 was at the downstream of a creek entrance to Pacific Ocean and partially covered by mangroves with conductivities fluctuated between about 28 mS cm$^{-1}$ and about 45 mS cm$^{-1}$, depending on the tidal actions.

Site #2 was located at the upstream of a freshwater creek surrounded by light industries with an almost constant conductivity of about 2.3 mS cm$^{-1}$ that does not affect by tidal actions.

1.6.1 Site #1

Sensor #1 was deployed at Site #1 together with a pH probe and a temperature sensor. During the 24 h deployment period, the conductivity, pH and temperature of the site water were varied between about 28 mS cm$^{-1}$ to about 45 mS cm$^{-1}$, from about 7.90 to about 8.09 and from about 21.2 to about 24.8° C., respectively. These changes are found to be strongly associated with tidal actions.

Figure 5A:
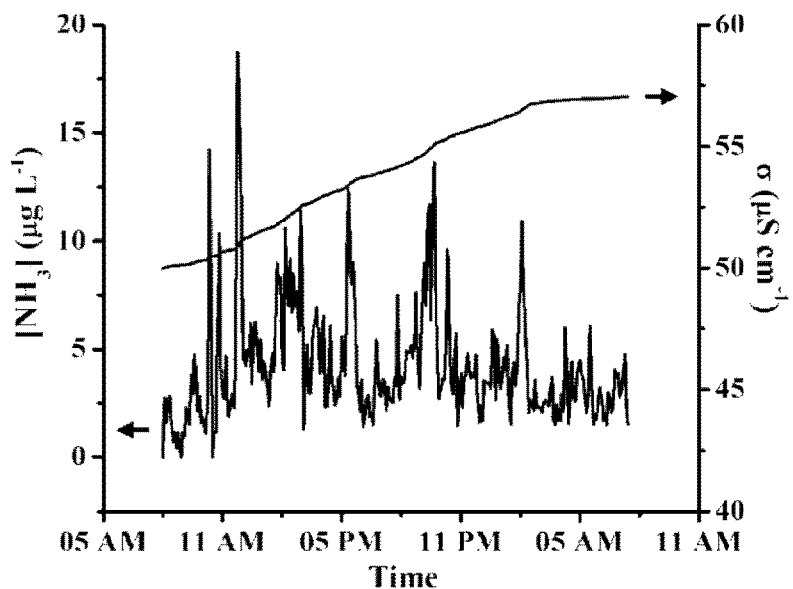
FIG. 5A shows the recovered σ-t profile and the corresponding instantaneous $NH_3$ concentration-time profile.

Increased conductivities and pHs with decreased temperatures were observed during high tide periods. FIG. 5A shows the recovered σ-t profile and the corresponding instantaneous NH$_3$ concentration changes real-time determined by Equation (4). This continuous NH$_3$ concentration profile exhibits a versatile change of NH$_3$ levels.

Figure 5B:
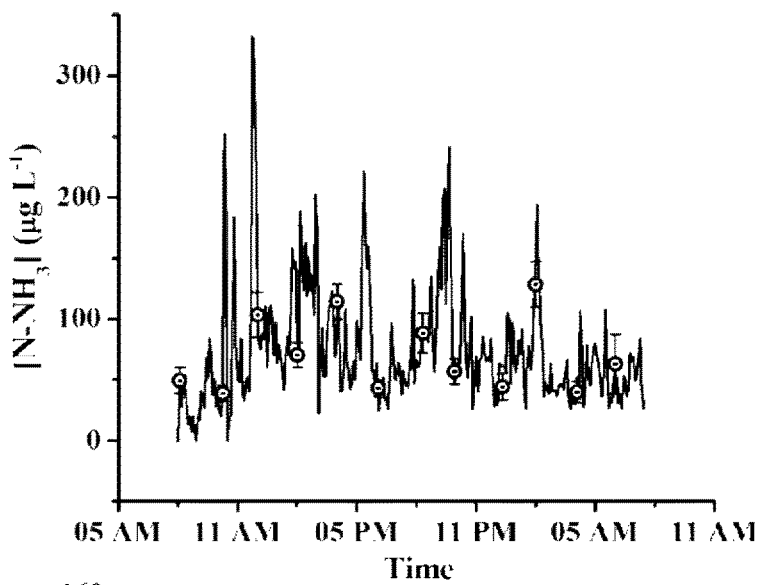
FIG. 5B shows $NH_4^+$ concentration-time profile (Red arrows indicating sampling points for laboratory analysis)

During the deployment, the two high tides occurred around 10 am and 10:30 pm, and the two low tides happened in 4:30 pm and 4 am the next day. Increased NH$_3$ concentrations were observed around these high and low tide points. This could be due to the tidal actions stirring up the precipitated NH$_3$/NH$_4^+$ in mangrove wetlands and creek sediments. Furthermore, over the 24 h deployment period, the total conductivity increment (dσ) derived from FIG. 5A was 10.2 µS cm$^{-1}$, an absolute average NH$_3$ concentration ($\overline{[NH_3]}_{Sample}$) of 5.25 µg L$^{-1}$ can therefore be obtained from Equation (6a). FIG. 5B shows the NH$_4^+$ profile over the deployment period determined by Equation (7). An absolute average NH$_4^+$ concentration ($\overline{[NH_4^+]}_{Sample}$) of about 75.3 µg L$^{-1}$ can be obtained by Equation (7) using $\overline{[NH_3]}_{Sample}$=5.25 µg L$^{-1}$. It should be noted that $K_b$ (25° C.)=1.75×10$^{-5}$ was used for all calculations.

Figure 5C:
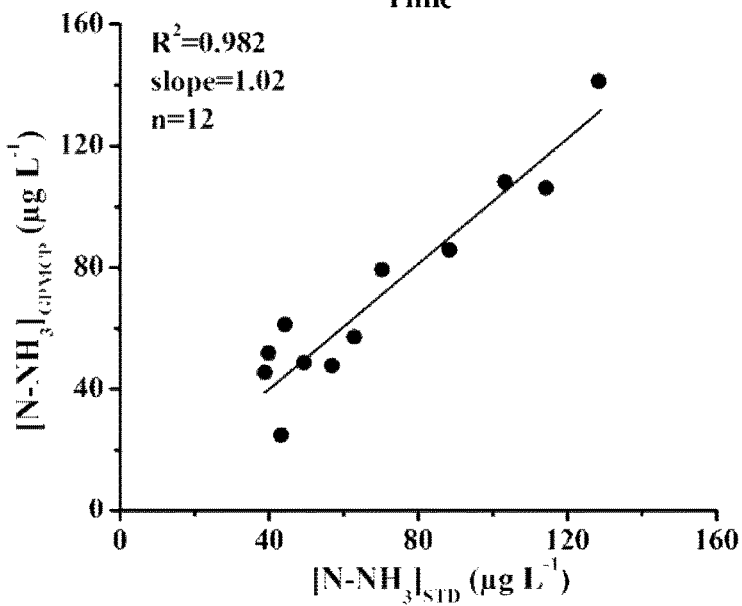
FIG. 5C shows a plot of $[NH_3—N]_{sensor}$ against $[NH_2—N]_{STD}$.

Considering that the temperatures were varied between about 21.2 and about 24.8° C. during the deployment period, errors will be introduced by using $K_b$ (25° C.) but should be less than about 5% because about 5° C. temperature changes will cause less than about 5% changes in $K_b$ values. During the deployment, water samples were collected every about 2 hours for laboratory determination of ammoniacal nitrogen ([NH$_3$—N]$_{STD}$) by the standard method. In the present case, the determined [NH$_3$—N]$_{STD}$ is equivalent to the concentration sum of NH$_3$ and NH$_4^+$. FIG. 5C shows a plot of total NH$_3$ and NH$_4^+$ concentrations ([NH$_3$—N]$_{sensor}$) determined by sensor against [NH$_3$—N]$_{STD}$. An almost unity slope value suggests an excellent agreement between the two methods.

1.6.2 Site #2

Site #2 was selected to represent typical freshwater creek unaffected by tidal action. The data from sensor #2 is shown in Table S2 in FIG. 13. The sensor #2 was deployed at Site #2 together with a pH probe and a temperature sensor. During the deployment period, the temperature of the site water was varied between about 20.6 to about 22.5° C., while conductivity (about 2.3 mS cm$^{-1}$) and pH (about 7.90) remained almost constant.

Figures 11A, 11B, 11C:
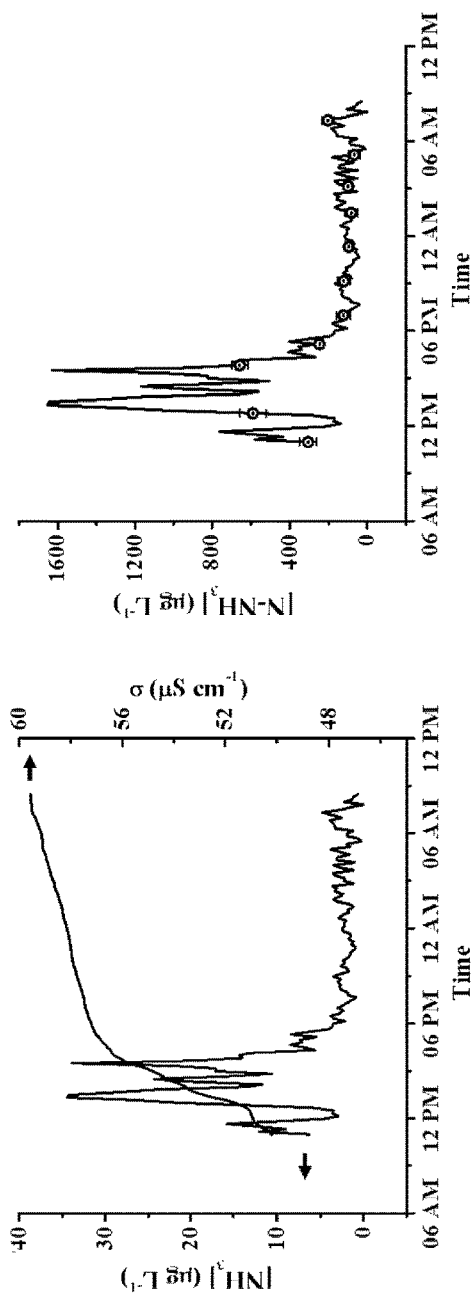
FIG. 11A to 11C shows that the field site was located at Loders Creek on Wardoo St, Gold Coast, Australia. It is close to the urban residential area and some light industries. The freshwater section of Loders Creek has been highly modified to manage stormwater, but the northern tributary still has a natural channel. Therefore, the northern tributary of Loders Creek was selected for this study. Water temperature is about 23.5-26° C., average water temperature is about 25° C., so the K constant under this temperature is found from above (i.e., 0.00123), water conductivity is about 2267.4 µS $cm^{-1}$, water pH is about 7.5-7.64, average water pH is about 7.57, so the concentration of $NH_4^+$ can be calculated by Equation (7), so the total ammonia nitrogen (N—$NH_3$) is the total concentration of $NH_3$ and $NH_4^+$.
Figure 12:
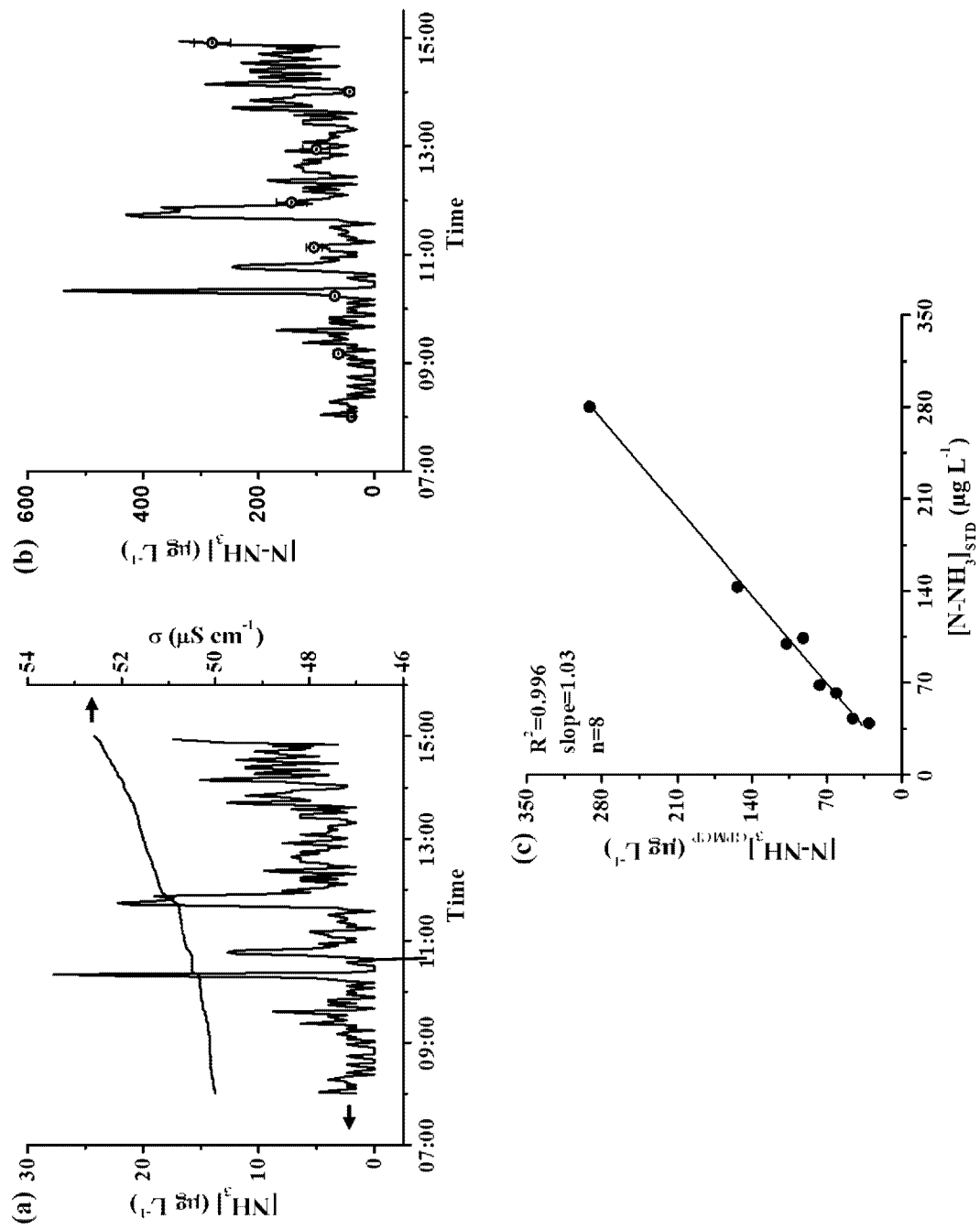
FIG. 12 shows that the field site was located at Guanaba Creek on Tarata Rd, Gold Coast, Australia. It is bordered by several horse ranches and a large area of grassland. Water temperature is about 20.6-22.5° C., average water temperature is about 21.1° C., so the K constant under this temperature is calculated from above (i.e., 0.00126), water conductivity about 1249.1 µS $cm^{-1}$, water pH is about 7.94-8.02, average water pH is about 7.98, the concentration of $NH_4^+$ can be calculated by Equation (7), so the total ammonia nitrogen (N—$NH_3$) is the total concentration of $NH_3$ and $NH_4^+$. The average N—$NH_3$ concentration calculated from MEAP is about 94.00 µg $L^{-1}$ over experiment period.
Figure 16:
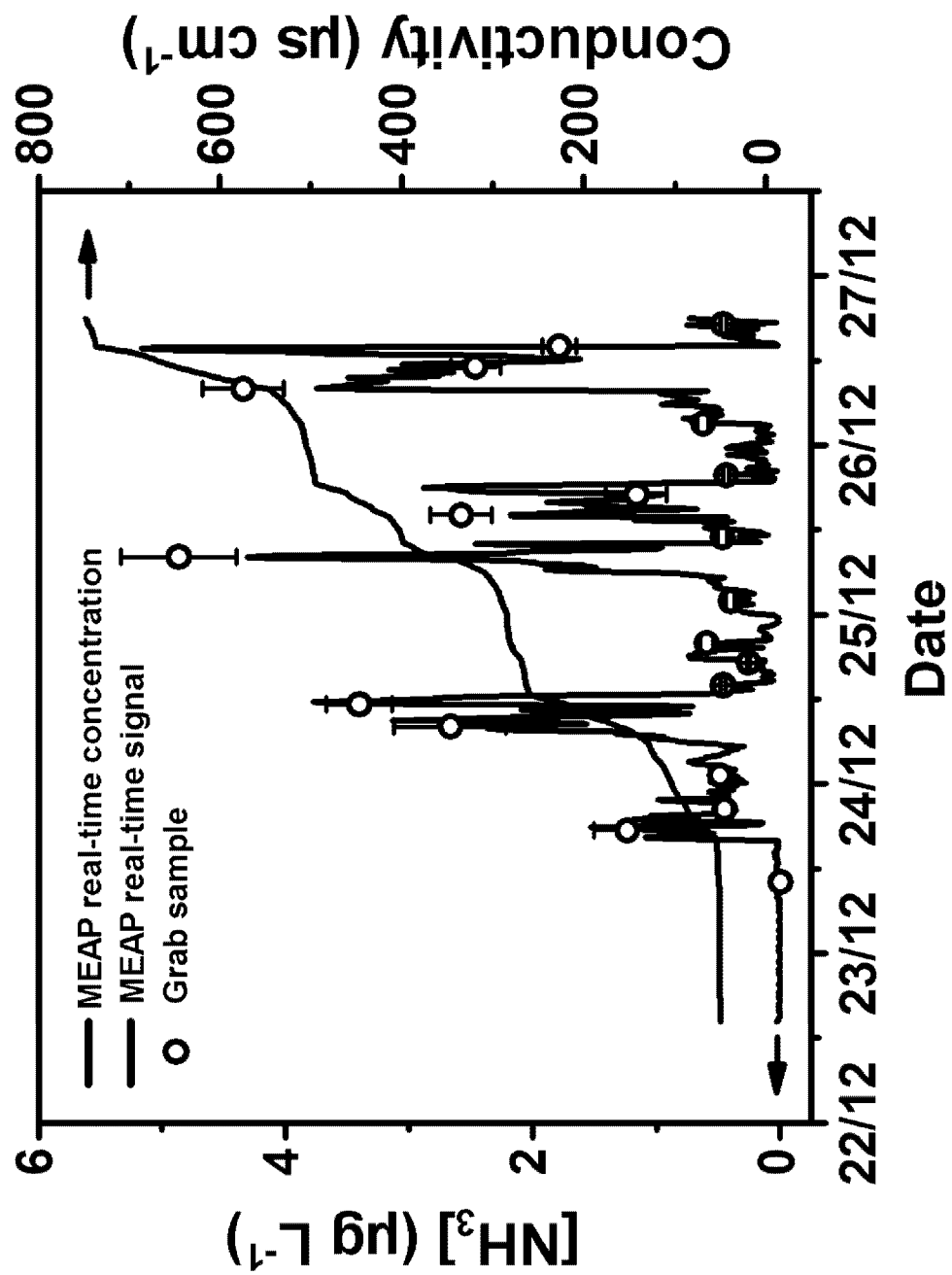
FIG. 16 shows real-time continuous gaseous $NH_3$ concentration profile obtained by our device and the $NH_3$ concentrations of grab samples by standard method from the soils of an agricultural land in Queensland, Australia over a 96 hour period.

Differing significantly to Site #1, the continuous $NH_3$ and $NH_4^+$ concentration profiles (FIGS. 11A and 11B) recorded over the deployment period showed high $NH_3/NH_4^+$ concentrations during daytime and very low concentrations during the night, suggesting that the high daytime $NH_3/NH_4^+$ levels could be attributed to the discharges into the creek from the surrounding industries. The plot of $[NH_3\text{—}N]_{sensor}$) against $[NH_3\text{—}N]_{STD}$ is given in FIG. 11C with an almost unity slope value, suggesting 1.6.3 Gaseous $NH_3$ Monitoring The sensor was used for real-time in situ monitoring of gaseous $NH_3$ concentration evaporated from soil (FIG. 16). At the time of experiment was conducted, the soil site was use to grow vegetables. The blank soil $NH_3$ evaporation was continuously monitored during the first 24-hour deployment. The ammonia containing fertilizer (about 4.78 g $NH_4Cl$) was then applied and pH was adjusted to about 7.0. The $NH_3$ evaporation was continuously monitored for the next 72 hours. The grab gas samples were collected every 3 hours during daytimes and analysed by standard method for validation. The green curve shows the real-time recorded conductivity changes, which can be used to obtain the average concentrations of evaporated $NH_3$ during the deployment period. After fertilizer was introduced, the average concentrations of evaporated $NH_3$ for the three consecutive days were about 0.278 $\mu g\ L^{-1}$, about 0.171 $\mu g\ L^{-1}$ and about 0.298 $\mu g\ L^{-1}$, respectively, which are correlated to the highest temperature of the day (the highest temperatures during the 3 consecutive deployment days were about 28.4° C., about 26.7° C. and about 29.4° C., respectively).

The real-time recorded conductivity changes can also be used to determine instantaneous $NH_3$ evaporation rate. The black curve shows instantaneous evaporated $NH_3$ concentration profile derived from the measured conductivity profile over a 72 hour deployment period. The instantaneous $NH_3$ evaporation rate was found to be highly correlated to the daily temperature changes. A higher the temperature results in a higher the instantaneous $NH_3$ evaporation rate can be observed and confirmed by the standard analyses of the grab samples. As such, the instantaneous $NH_3$ evaporation rates increase during morning, peak around the noon and decrease in the afternoon, except in Date 25/12, because the sudden quick rainfall in that afternoon.

1.6.4 3D Deployment of the Sensor

The analytical device (DGT device) (sensor) was deployed at targeted locations for free ammonia measurement. FIGS. 15A and 15B illustrates two exemplary deployment strategies to serve different needs. The planar deployment strategy in FIG. 15A may be useful to acquire the 2-dimensional free ammonia concentration distribution at the same depth. The vertical deployment strategy of FIG. 15B may enable the acquisition of 1-dimensional free ammonia concentration distribution along a vertical water column. These strategies could be applied individually or combined to provide 3-dimensional free ammonia concentration distribution profile.

While the invention has been described with reference to preferred embodiments above, it will be appreciated by those skilled in the art that it is not limited to those embodiments, but may be embodied in many other forms, variations and modifications other than those specifically described. The invention includes all such variation and modifications. The invention also includes all of the steps, features, components and/or devices referred to or indicated in the specification, individually or collectively and any and all combinations or any two or more of the steps or features.

In this specification, unless the context clearly indicates otherwise, the term "comprising" has the non-exclusive meaning of the word, in the sense of "including at least" rather than the exclusive meaning in the sense of "consisting only of". The same applies with corresponding grammatical changes to other forms of the word such as "comprise", "comprises" and so on.

Although the invention has been described with reference to particular chemicals, these identified chemicals should be only regarded as examples within their particular chemical family as opposed to a complete and exhaustive list of possible constituents. The skilled person will appreciate that unless otherwise specified, the mere substitution of one particular chemical for another with similar uses, effect, chemical formulae, pharmaceutical capability, biological compatibility or otherwise similar properties falls within the scope or object of the invention described herein, and that the scope of the invention includes any and all of these substitute chemicals insofar as the object of the invention is still fulfilled.

Any discussion of prior art information in this specification is not to be taken as any form of acknowledgement that that prior art information would be considered common general knowledge by a person of skill in the art, either in Australia or in any foreign country.

The invention claimed is:

1. A sensor for in situ detection of a target chemical species, the sensor comprising:
a gas permeable membrane having a sampling side and an opposing analytical side, wherein the sampling side of the gas permeable membrane is capable of receiving a sample and the gas permeable membrane is permeable to target chemical species present in the sample;
a reservoir of a weak acid or a weak base in contact with the analytical side of the gas permeable membrane;
a conductivity detector located in the reservoir for measuring a conductivity on the analytical side of the gas permeable membrane;
wherein the target chemical species present in the sample passes through the gas permeable membrane and reacts with the weak acid or the weak base thereby generating ionic species, the presence of which changes the conductivity at the analytical side of the gas permeable membrane.

2. The sensor according to claim 1, wherein, prior to use of the sensor, the weak acid or weak base in the reservoir has a conductivity of at most about 500 $\mu S\ cm^{-1}$.

3. The sensor according to claim 2, wherein the weak acid is disposed on the analytical side of the gas permeable membrane and includes boric acid.

4. The sensor according to claim 3, wherein the gas permeable membrane is a hydrophobic polytetrafluoroethylene ("PTFE") membrane.

5. A sensor for in situ detection of free ammonia, the sensor comprising:
a gas permeable hydrophobic PTFE membrane having a sampling side and an opposing analytical side, wherein the sampling side of the gas permeable hydrophobic PTFE membrane is capable of receiving a sample and the gas permeable hydrophobic PTFE membrane is permeable to free ammonia present in the sample, and wherein a reservoir of boric acid is present on the analytical side of the gas permeable hydrophobic PTFE membrane;
a conductivity detector located in the reservoir in contact with the boric acid, and including an electrode for detecting a change in conductivity on the analytical side of the gas permeable hydrophobic PTFE membrane;

wherein during an operative state of the gas permeable hydrophobic PTFE membrane, free ammonia present in the sample passes through the gas permeable hydrophobic PTFE membrane and reacts with the boric acid thereby generating ionic species, the presence of which increases the conductivity at the analytical side of the gas permeable hydrophobic PTFE membrane.

6. The sensor according to claim 5, wherein the gas permeable hydrophobic PTFE membrane is supported in a housing having defined therein an opening to allow the sample to be received onto the face of the sampling side of the membrane.

7. The sensor according to claim 5, wherein the sensor is capable of determining at least about 1 µg $L^{-1}$ of the target chemical species in a solution.

8. The sensor according to claim 5, wherein the change in conductivity at the analytical side of the membrane is detected at levels as low as about 0.5 µS/cm.

9. A system for the in situ detection of a target chemical species in water, the system comprising:
- a support structure under the water for supporting a plurality of sensors;
- a floater on the surface of the water from which the plurality of sensors depend,
- an anchor to keep the plurality of sensors under the water;
- a data acquisition unit for receiving data from the plurality of sensors;
- wherein the plurality of sensors are spaced from one another under the water in a series so that a 3-dimensional profile of a concentration of the target chemical species in the water can be formed from the data received by the data acquisition unit; and
- wherein the sensor includes:
  - a gas permeable membrane having a sampling side and an opposing analytical side, wherein the sampling side of the gas permeable membrane is capable of receiving a sample and the gas permeable membrane is permeable to target chemical species present in the sample;
  - a reservoir of a weak acid or a weak base in contact with the analytical side of the gas permeable membrane;
  - a conductivity detector in the reservoir for measuring a conductivity on the analytical side of the gas permeable membrane;
  - wherein the target chemical species present in the sample passes through the gas permeable membrane and reacts with the weak acid or the weak base thereby generating ionic species, the presence of which changes the conductivity at the analytical side of the gas permeable membrane.

10. The system according to claim 9, wherein at least one of the sensors is arranged to detect the target chemical species, and the data acquisition unit has programmed therein a pre-determined threshold concentration of the target chemical species;

wherein the data acquisition unit compares any detected concentration of the target chemical species as measured by the at least one of the sensors to the pre-determined threshold concentration for the target chemical species and raises an alert if the difference between the two exceeds a pre-determined level.

11. The system according to claim 10, wherein the data acquisition unit is a part of a programmable logic controller ("PLC") that also controls a process that is capable generating the target chemical species.

12. The system according to claim 11, wherein upon raising the alert, the PLC takes at least one step to change at least one step in the process that changes the concentration of the target chemical species generated by the process.

* * * * *